United States Patent
Chaput et al.

(10) Patent No.: US 11,155,792 B2
(45) Date of Patent: Oct. 26, 2021

(54) HIGHLY SENSITIVE OPTICAL SENSOR FOR POLYMERASE SCREENING

(71) Applicant: ARIZONA BOARD OF REGENTS ON BEHALF OF ARIZONA STATE UNIVERSITY, Scottsdale, AZ (US)

(72) Inventors: John Chaput, Irvine, CA (US); Andrew Larsen, Scottsdale, AZ (US); Matthew Dunn, Scottsdale, AZ (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 0 days.

(21) Appl. No.: 16/789,278

(22) Filed: Feb. 12, 2020

(65) Prior Publication Data
US 2020/0190488 A1    Jun. 18, 2020

Related U.S. Application Data

(62) Division of application No. 15/766,716, filed as application No. PCT/US2016/056305 on Oct. 10, 2016, now Pat. No. 10,584,319.

(60) Provisional application No. 62/239,178, filed on Oct. 8, 2015.

(51) Int. Cl.
| | | |
|---|---|---|
| *C12N 9/12* | (2006.01) | |
| *C12Q 1/68* | (2018.01) | |
| *G01N 21/64* | (2006.01) | |
| *B01L 3/00* | (2006.01) | |

(52) U.S. Cl.
CPC ......... *C12N 9/1252* (2013.01); *C12N 9/1241* (2013.01); *C12Q 1/68* (2013.01); *G01N 21/64* (2013.01); *B01L 3/5027* (2013.01); *C12Y 207/07007* (2013.01)

(58) Field of Classification Search
CPC .......... C12Y 207/07007; C12N 9/1252; C12N 9/1241; B01L 3/5027; G01N 21/64; C12Q 1/68
See application file for complete search history.

(56) References Cited

U.S. PATENT DOCUMENTS

| | | | | |
|---|---|---|---|---|
| 9,347,095 B2 * | 5/2016 | Regan | ................. | C12Q 1/6858 |
| 9,469,862 B2 * | 10/2016 | Chaput | ................. | C12P 7/34 |
| 2015/0191707 A1 * | 7/2015 | Behlke | ................. | C12N 9/1252 |
| | | | | 435/91.2 |

OTHER PUBLICATIONS

Aharoni et al., High-throughput screens and selection of enzyme-encoding genes. Curr. Opin. Chem. Biol., 2005, vol. 9: 210-216. (Year: 2005).*
Miller et al., Directed evolution by in vitro compartmentalization. Nature Methods, 2006, vol. 3(7): 561-570. (Year: 2006).*
Tawfik et al., Man-made cell-like compartments for molecular evolution. Nature Biotechnol., 1998, vol. 16: 652-656. (Year: 1998).*

* cited by examiner

*Primary Examiner* — Ganapathirama Raghu
(74) *Attorney, Agent, or Firm* — Rodney J. Fuller; Booth Udall Fuller, PLC

(57) ABSTRACT

The present invention is directed to a polymerase activity assay that produces a strong optical signal when a primer-template complex is extended to full-length product. The assay uses Cy3 as the molecular beacon and Iowa Black® RQ as the quencher. The signal-to-noise-ratio (STNR) of this donor-quencher pairing is ~200-fold over background, which is considerably better than other donor-quencher pairs (STNRs ~10-20-fold). The STNR allows for solution-based monitoring of polymerase activity. Because the sensor functions via Watson-Crick base pairing, the polymerase activity assay may also be used to evolve polymerases to accept xeno nucleic acids as substrates.

20 Claims, 11 Drawing Sheets
Specification includes a Sequence Listing.

HIGHLY SENSITIVE OPTICAL SENSOR FOR POLYMERASE SCREENING

CROSS REFERENCE TO RELATED APPLICATIONS

This application is a divisional of U.S. patent application Ser. No. 15/766,716, filed Apr. 6, 2018 (issued as U.S. Pat. No. 10,583,319), which is the U.S. National Stage of International Application No. PCT/US2016/056305, filed Oct. 10, 2016, which claims the benefit of U.S. Provisional Patent Application No. 62/239,178, filed Oct. 8, 2015, the contents of each of which are herein incorporated by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 14,202 byte ASCII (text) file named "SeqList" created on Oct. 5, 2016.

GOVERNMENTAL SUPPORT OF APPLICATION

This invention was made with government support under N66001-14-2-4054 awarded by the Department of Defense. The government has certain rights in the invention.

TECHNICAL FIELD

This disclosure relates to methods of screening polymerase activity, in particular, xeno-nucleic acid polymerase activity.

BACKGROUND

Recent advances in polymerase engineering have made it possible to synthesize nucleic acid polymers with a wide range of chemical modifications, including xeno-nucleic acid (XNA) polymers with backbone structures that are not found in nature[1-3]. While this technological advance generated significant interest in XNA polymers as a synthetic polymer for future applications in molecular medicine, nanotechnology, and materials science[4-7], the current generation of XNA polymerases function with markedly lower activity than their natural counterparts[8,9]. The prospect of developing synthetic polymerases with improved activity and more diverse functions has driven a desire to apply molecular evolution as a strategy for altering the catalytic properties of natural polymerases[10,11]. Compartmentalized self-replication (CSR) and compartmentalized self-tagging (CST) are examples of technologies that have been developed to evolve polymerases with expanded substrate specificity[1,12.] However, these methods use the parent plasmid as template for the primer-extension reaction, which limits the range of polymerase functions to enzymes that promote DNA-templated synthesis. Thus, progress in the realm of synthetic biology is hindered by the lack of effective XNA polymerase. Accordingly, there is a need for methods of developing XNA polymerases with activity comparable to their natural counterparts.

SUMMARY OF THE INVENTION

Provided are methods of assaying the activity of a target polymerase. The methods comprise expressing the target polymerase in a competent cell, for example an *E. coli* cell, and encapsulating the competent cell expressing the target polymerase in a water/oil droplet comprising reagents required for nucleotide synthesis on a DNA primer/template complex. The methods then comprise lysing the competent cell in the water/oil droplet to release the target polymerase; incubating the water/oil droplet to allow the polymerase to assemble nucleoside triphosphates according to the template; emulsifying the water/oil droplet in a bulk aqueous phase to generate a water/oil/water droplet; and detecting the level of fluorescence in the water/oil/water droplet, wherein the level of fluorescence is indicative of the activity of the target polymerase.

Also provided are methods of evolving natural polymerases to accept xeno nucleic acids as substrates. The methods comprise expressing a mutated polymerase in a competent cell, for example an *E. coli* cell, wherein the mutated polymerase comprises a mutation in an amino acid residue with a propensity to affect substrate specificity, and encapsulating the competent cell expressing the mutated polymerase in a water/oil droplet. The methods then comprise lysing the competent cell in the water/oil droplet to release the mutated polymerase; incubating the water/oil droplet to allow the mutated polymerase to assemble triphosphates of xeno nucleic acids according to the template; emulsifying the water/oil droplet in a bulk aqueous phase to generate a water/oil/water droplet; and isolating the water/oil/water droplet if the water/oil/water droplet has a level of fluorescence that is at least 10 folds over background. In some implementations, expressing a mutated polymerase in a competent cell comprises generating a mutation in a natural polymerase-encoding DNA sequence that results in a substitution mutation at the amino acid residue with a propensity to affect substrate specificity and introducing the mutated natural polymerase-encoding DNA sequence into the genome of the competent cell.

For both methods of the invention, the encapsulation the competent cell expressing the target polymerase in a water/oil droplet results in the water/oil droplet comprising at most a single competent cell. In both methods, the reagents in the water/oil droplet comprise nucleoside triphosphates and an optical reporter, which comprises a primer, a template, a fluorophore, and a quencher. The quencher comprises a modification at the 5' or 3' end. In one embodiment, the fluorphore is Cy3 and the quencher is Iowa Black RQ. In some aspects, a hydrophilic microfluidic device is used to emulsify the water/oil droplet in a bulk aqueous phase to generate a water/oil/water droplet. In some implementations, the hydrophilic microfluidic chip comprises a single inlet flow focusing junction geometry of 14×17 μm.

In some embodiments, methods of evolving natural polymerases to accept xeno nucleic acids as substrates further comprises sorting the water/oil/water droplet by the level of fluorescence prior to isolating water/oil/water droplets. In some implementations, the water/oil/water droplet is sorted using a fluorescence-activated cell sorter.

In some aspects, introducing the mutated natural polymerase-encoding DNA sequence into the genome of the competent cell comprises transforming the competent cell with a plasmid comprising the mutated natural polymerase-encoding DNA sequence. These embodiments of the methods of evolving natural polymerases to accept xeno nucleic acids as substrates further comprises extracting the plasmid encoding the mutated polymerase from the isolated water/oil/water droplets having a level of fluorescence in the water/oil/water droplet is at least 10 folds over background and transforming a new population of competent cells with the extracted plasmid. The method may further comprise expressing the mutated polymerase encoded by the extracted plasmid and assaying the function of the mutated polymerase with triphosphates of xeno nucleic acids as substrates.

In some implementations of methods of evolving natural polymerases to accept xeno nucleic acids as substrates, the mutated polymerase originates from *Thermococcus* sp. 9° N. In this embodiment, the amino acid residue with a propensity to affect substrate specificity is selected from the group consisting of: residue 409, residue 485 and residue 664 of the *Thermococcus* sp. 9° N polymerase.

For the methods of evolving natural polymerases to accept xeno nucleic acids as substrates, the triphosphates of xeno nucleic acids may be α-L-threofuranosyl nucleic acid triphosphates.

In some implementations of the methods of the invention, a fluorophilic microfluidic chip encapsulates the competent cell expressing the target polymerase or the mutated polymerase in a water/oil droplet. The fluorophilic microfluidic chip comprises a single inlet flow focusing junction geometry of 14×17 µm. In some aspects, the fluorophilic microfluidic chip comprises a single inlet flow that is coated with a hydrophobic coating. In some implementations, the water/oil droplet has a diameter of about 14 µm or a volume of 1 pL.

In some implementations of both methods of the invention, competent cell in the water/oil droplet is lysed by incubation at 90° C., for example, by incubation at 90° C. for 5 minutes.

In some aspects, incubating the water/oil droplet to allow the polymerase to assemble nucleoside triphosphates according to the template takes place at 55° C. to allow the target polymerase or the mutated polymerase to assemble nucleoside triphosphate or triphosphates of xeno nucleic acids according to the template. For example, the water/oil droplet is incubated at 55° C. for at least 3 hours. In some implementations, the water/oil droplet is incubated at 55° C. for 18 hours.

Negative control: no NTPs. Positive control: dNTPs or no DNA-quencher probe. Panel E shows single-emulsion droplets containing a functional 9n-GLK polymerase that extends a primer-template complex with RNA (top) and non-functional (bottom) wild type 9n polymerase. The panel shows a cartoon depiction of the droplet, a brightfield micrograph of encapsulated *Escherichia coli* (arrow), a fluorescence micrograph of the same field of view, and an overlay of the two images. Scale bars represent 10 Panel F depicts flow cytometry analysis of 9n and 9n-GLK polymerases following NTP extension in water-in-oil-in-water (w/o/w) droplets.

Figure 2:
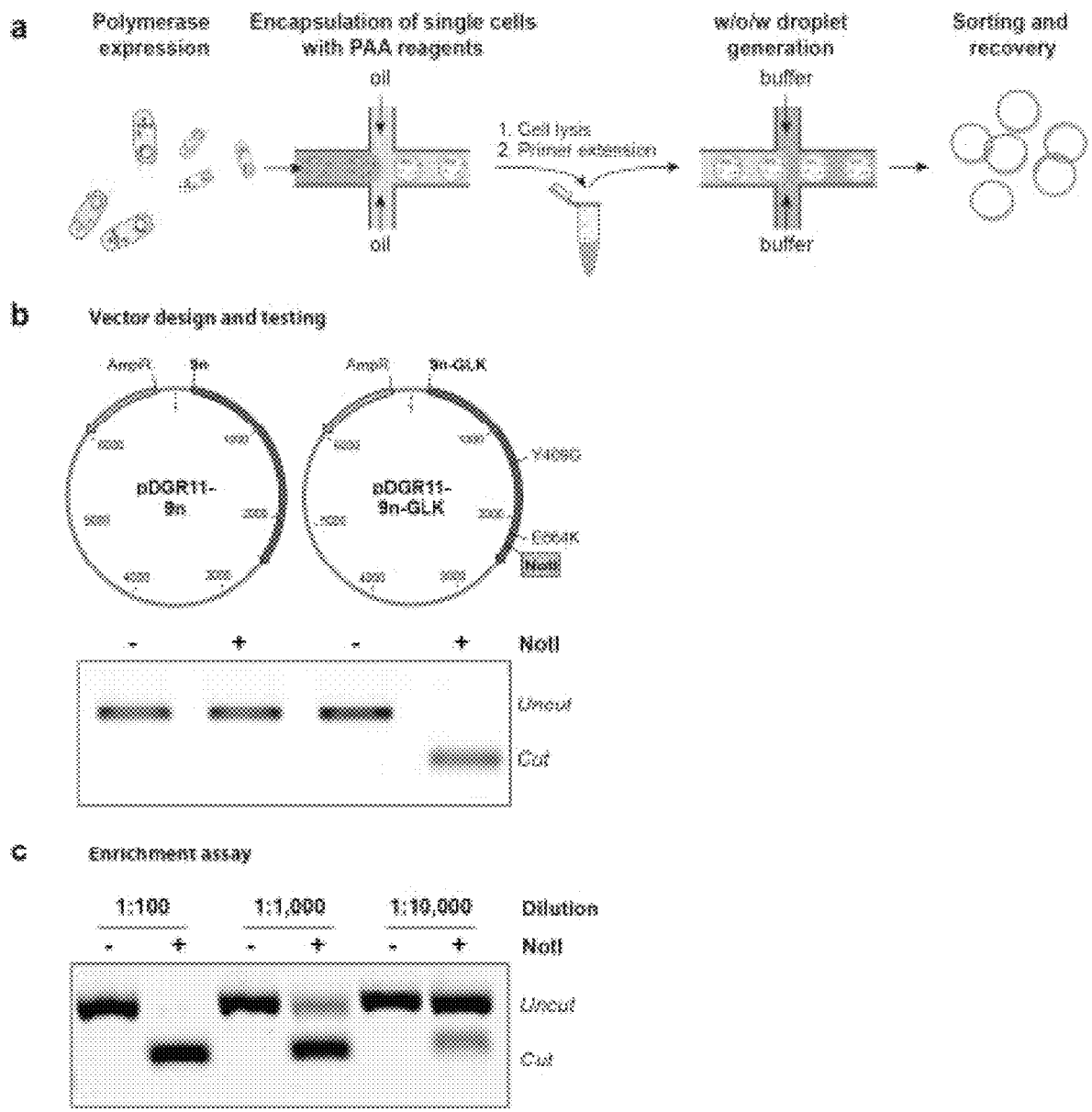

FIG. 2 depicts model selection of an engineered polymerase with RNA synthesis activity. Panel A is an overview of the microfluidic polymerase enrichment strategy. A pool of polymerase genes containing functional (green) and non-functional (blue) members are expressed in *E. coli* and encapsulated in water-in-oil (w/o) droplets generated in a microfluidics device. Polymerases are liberated from their bacteria by heat lysis and incubated at 55° C. to allow for primer extension. Using a second microfluidics device, droplets are emulsified into a bulk aqueous phase to generate w/o/w compartments. Fluorescent w/o/w compartments are sorted by Fluorescence-activated cell sorting (FACS), and the vectors encoding functional polymerases are recovered. Panel B shows the design of vectors encoding functional polymerases are recovered. The 9n-GLK vector was engineered to contain a unique NotI restriction site. Control digestion showing that NotI only cuts PCR-amplified DNA from the 9n-GLK vector. Panel C depicts the results of an enrichment assay. Following a complete cycle of selection and amplification (see FIG. 4), PCR-amplified DNA was digested with NotI to measure the enrichment of 9n-GLK from libraries that were doped at levels of 1:100, 1:1,000, and 1:10,000 (9n-GLK to 9n). NotI digestion of the PCR amplified DNA reveals an enrichment of ~1,200-fold per round of microfluidics selection.

Figure 3:
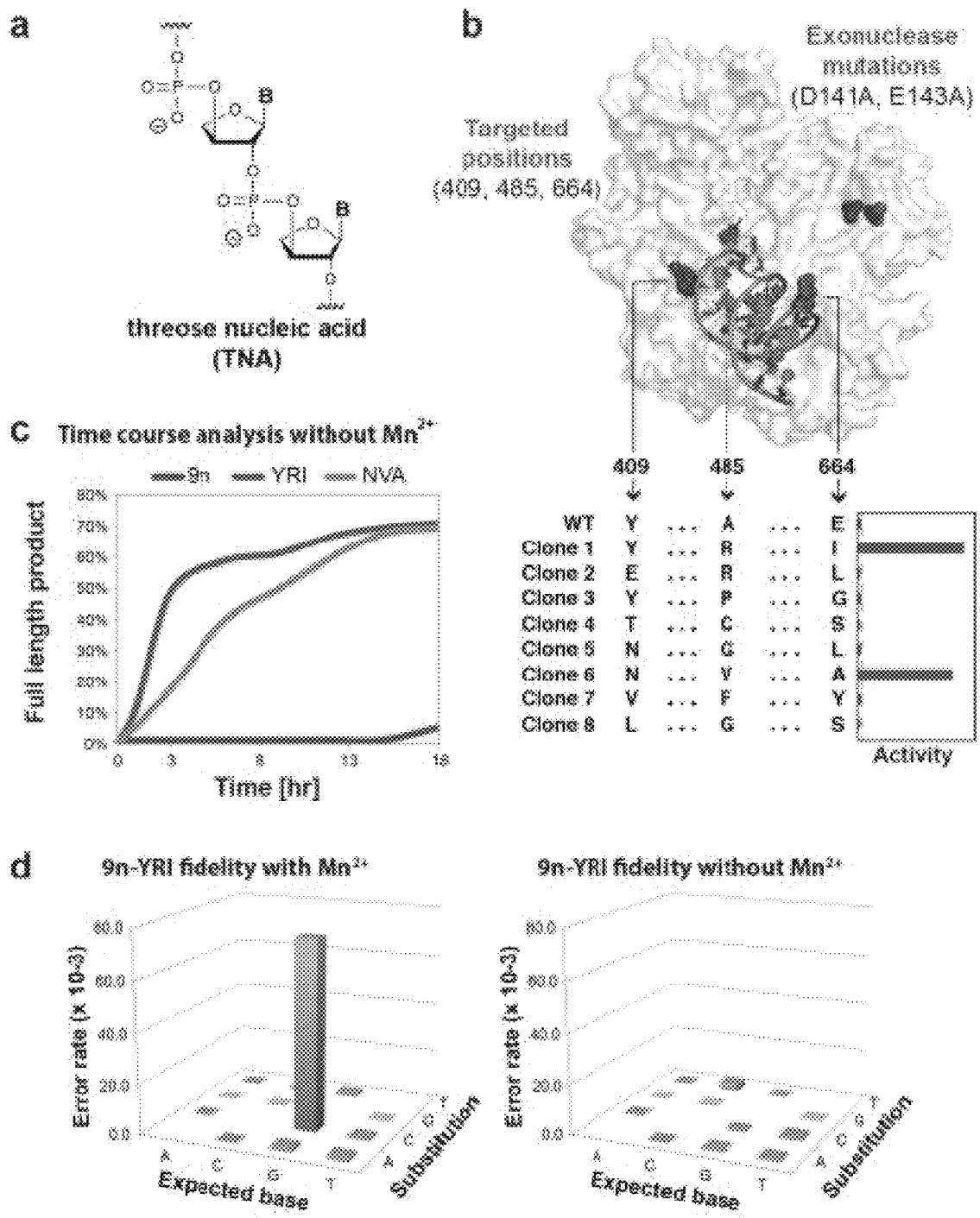

FIG. 3 depicts selection of a $Mn^{2+}$-independent threose nucleic acid (TNA) polymerase from a focused library. Panel A shows constitutional structure for the linearized backbone of TNA. Panel B shows mapping of positions 409, 485, and 664 onto the structure of 9n DNA polymerase (PDB: 4K8X). Polymerases isolated after one round of selection were analyzed for TNA synthesis activity in the absence of $Mn^{2+}$. Activity is defined as the amount of full-length product generated in 18 hrs. Basal activity of wild type 9n polymerase (dashed grey line). Panel C shows the time course of TNA synthesis for 9n-YRI and 9n-NVA polymerases compared to wild type 9n. Panel D depicts fidelity analysis of 9n-YRI polymerase in the presence and absence of manganese ions yields a mutational profile of 8 errors per 100 bases and 2 errors per 1000 bases, respectively.

Figure 4:
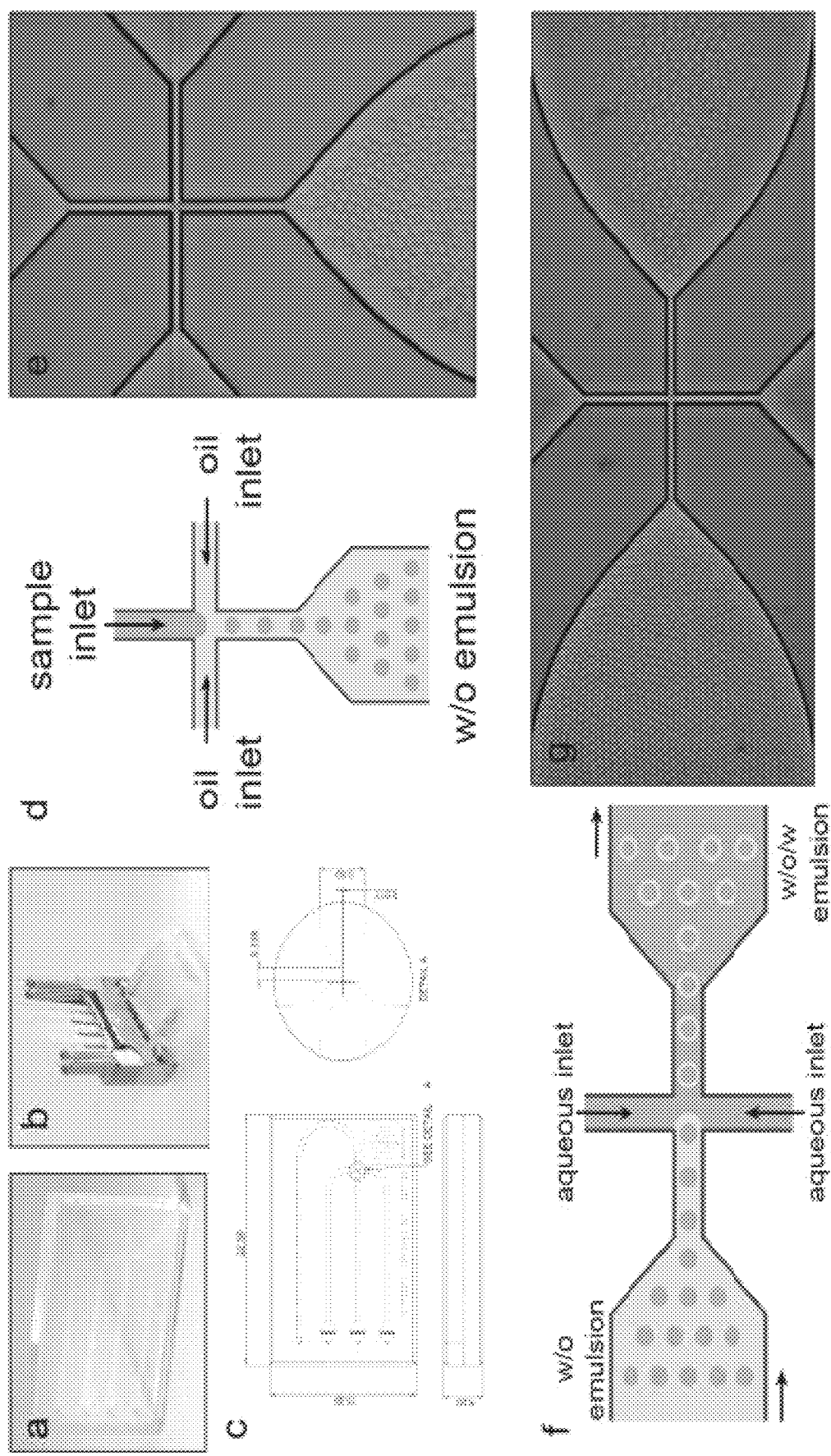

FIG. 4 depicts schematic and photographs of microfluidic chips and droplet formation. Panels A and B show a photograph of microfluidic chip with and without the syringe interface, respectively. Panel C is a CAD drawing detailing chip and junction dimensions. Panels A-C are provided courtesy of Dolomite Microfluidics. Panels D and E are a schematic and a photograph, respectively, of the fluorophilic droplet chip producing w/o emulsions. Panels F and G are a schematic and a photograph, respectively, of the hydrophilic chip that converts a water-in-oil emulsion in bulk oil phase to a water-in-oil-in-water (w/o/w) emulsion in bulk aqueous phase.

Figure 5:
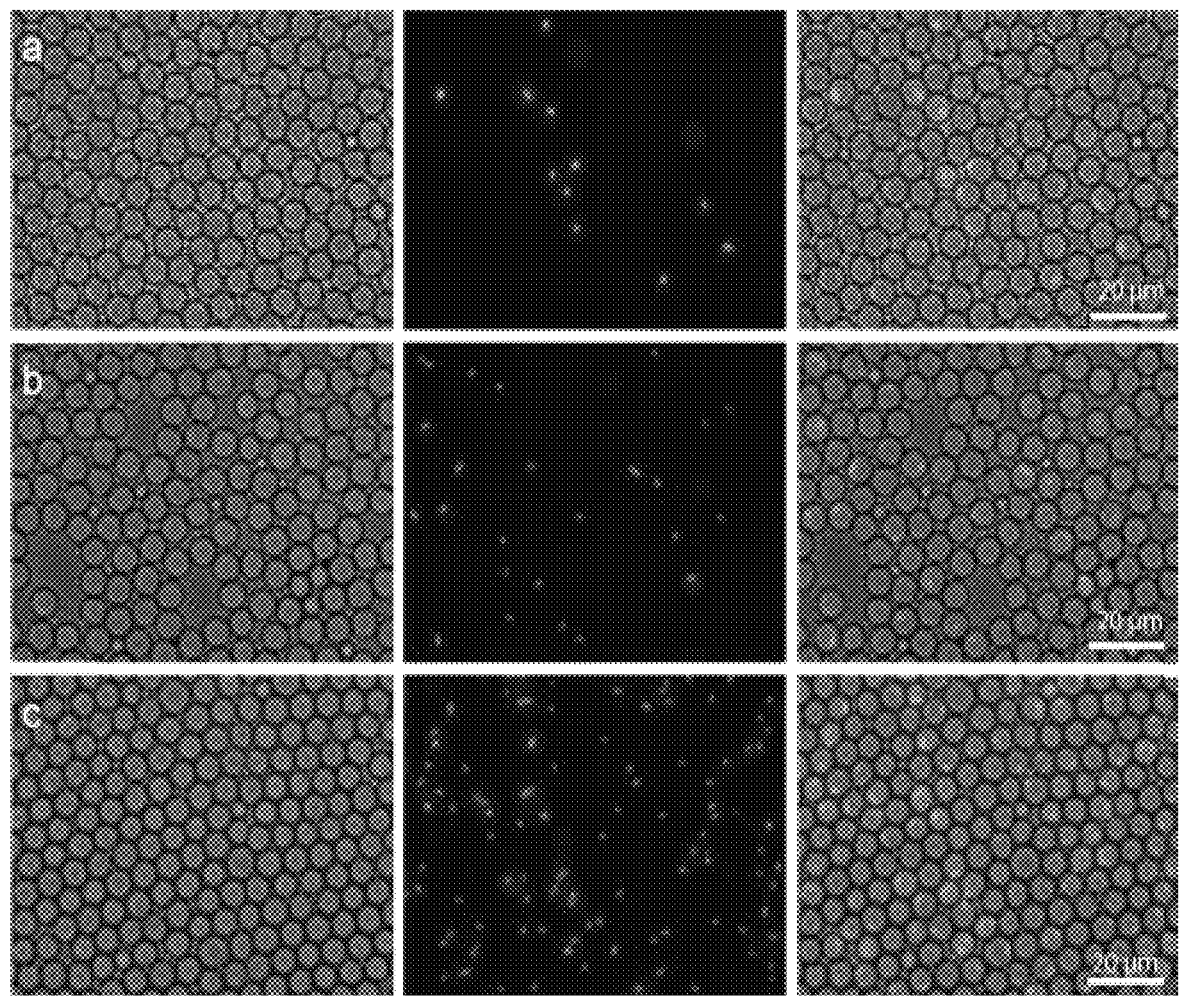

FIG. 5 depicts *E. coli* titration to confirm droplet occupancy. Green fluorescent protein (GFP)-expressing bacteria poised at an OD-600 of 0.5 (Panel A), 1.0 (Panel B), and 2.0 (Panel C) were encapsulated in w/o droplets. Representative bright field, fluorescence, and overlay images of the w/o droplets are shown (left to right). Average occupancy was determined by counting the number of fluorescent bacteria per droplet.

Figure 6:
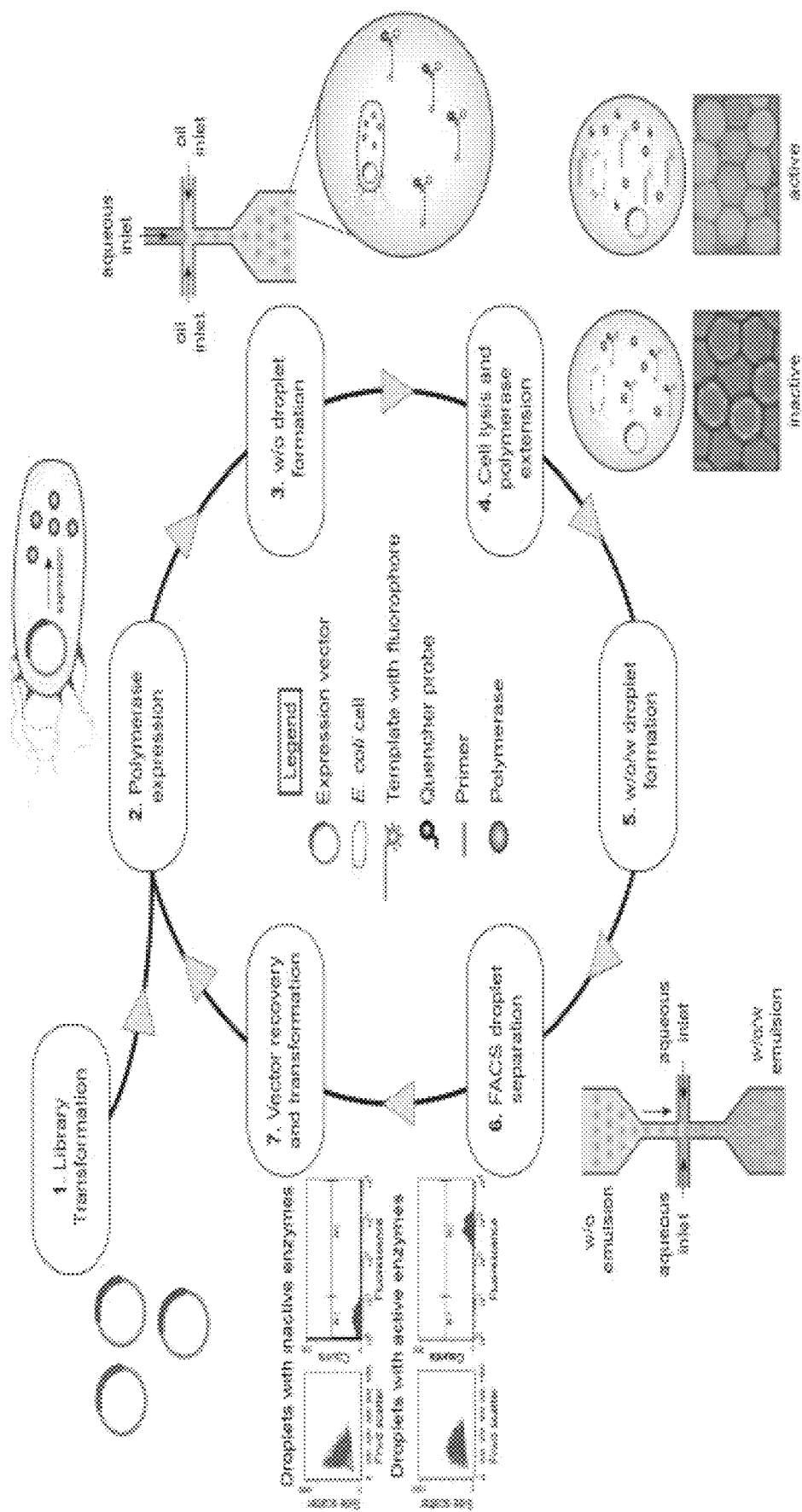

FIG. 6 depicts the polymerase evolution strategy developed for droplet microfluidics (DrOPS). Step 1: A library of DNA polymerase variants is transformed into *E. coli*. Step 2: The *E. coli* cells are grown to log phase in liquid media and induced with IPTG. Step 3: w/o droplets are generated microfluidically to produce a population of artificial compartments that contain on average one *E. coli* cell per occupied compartment and a fluorescence-based polymerase activity assay. Step 4: Polymerases are released from the *E. coli* by heat-induced lysis. The droplets are then incubated at 55° C. during which time the polymerases are challenged to extend the primer-template complex. At this point, qualitative analysis of the population can be performed by fluorescence and bright field microscopy. Step 5: The w/o droplets are then passed through a second microfluidic device to generate w/o/w emulsions in a bulk aqueous phase. Step 6: FACS is used to isolate droplets that generate strong fluorescence due to the activity of a functional polymerase. Step 7: Encoding plasmid DNA is recovered from sorted droplets by aqueous extraction and transformed into a new population of *E. coli* to initiate another round of selection or analyzed by DNA sequencing.

Figure 7:
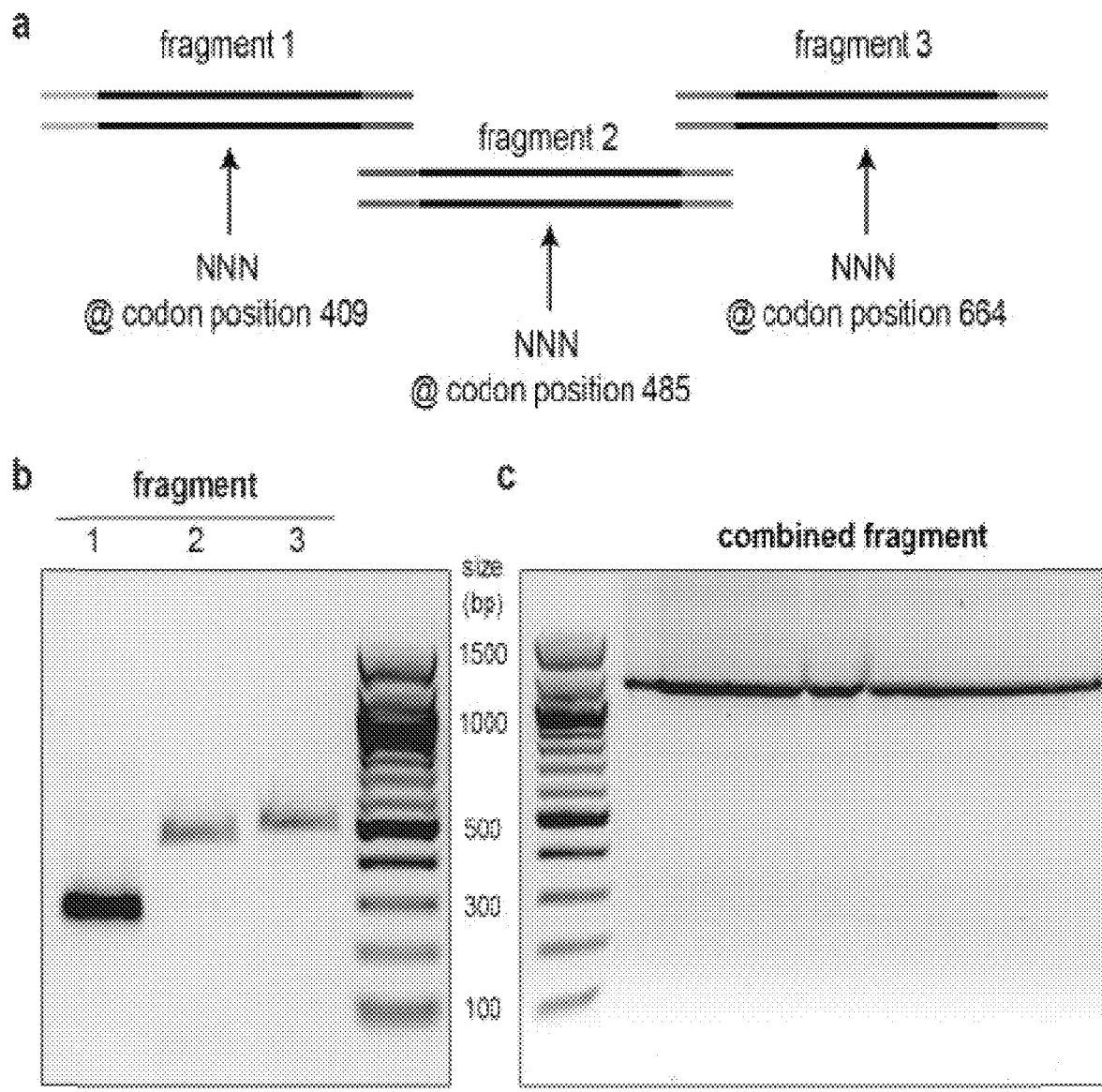

FIG. 7 depicts the generation of a focused polymerase library. Panel A shows three gBlock dsDNA fragments spanning the entire finger, palm, and thumb domains of 9n DNA polymerase were purchased from IDT with fully degenerate codons at positions 409, 485 and 664. Each fragment contained a complementary region for overlapping PCR. Panel B shows that each of the three fragments was individually amplified. Panel C shows the amplicons from each fragment were combined into a single PCR reaction using the forward primer for fragment one and the reverse primer for fragment three. The full-length fragment was combined with the remaining polymerase by restriction digestion, ligation and transformation.

Figure 8:
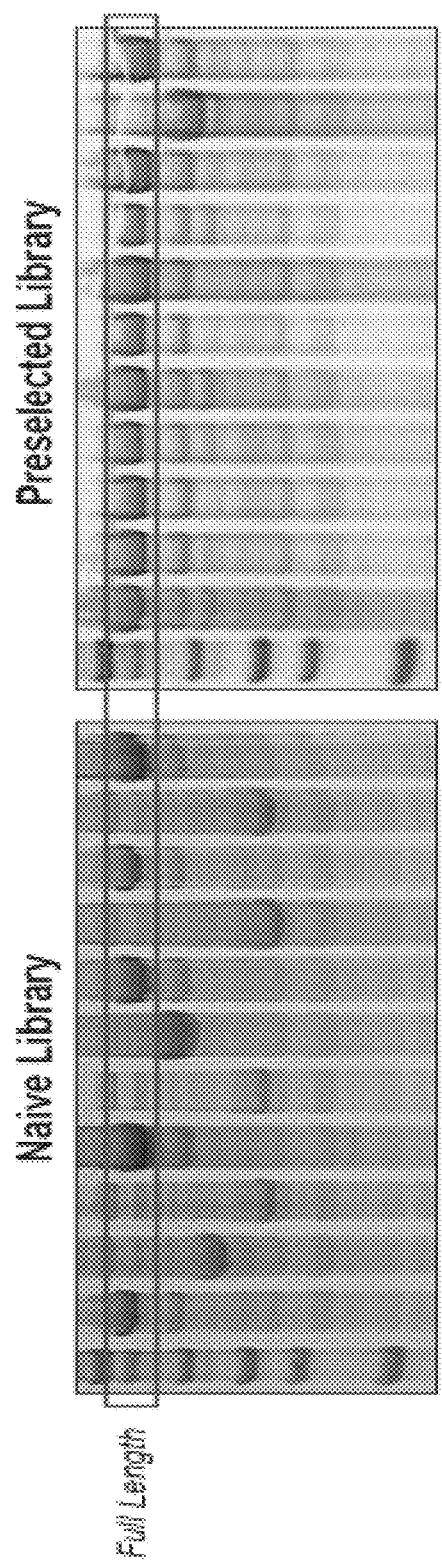

FIG. 8 depicts neutral drift selection for functional polymerases. One round of DrOPS was performed on the focused library in the presence of natural dNTP substrates to eliminate non-functional members. Denaturing PAGE analysis of 10 members from the naïve library (left) and the pre-selected library (right). Wild type 9n DNA polymerase was run in the first lane next to the ladder. Full-length products indicated by the red box.

Figure 9:
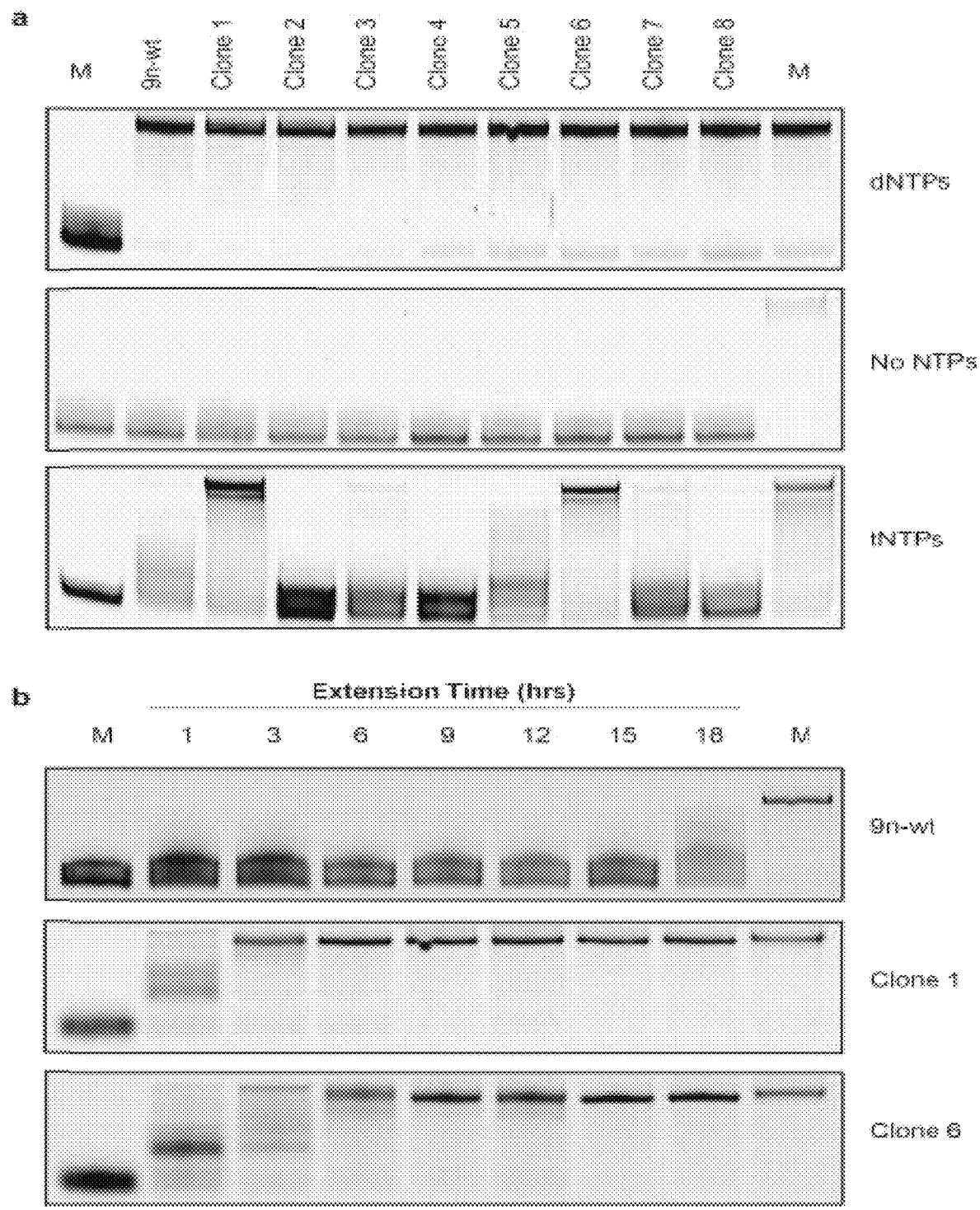

FIG. 9 depicts exemplary results of manganese-independent polymerase activity assays. All assays were completed with PBS2-IR800 DNA primer and ST.1G DNA template. Marker lanes (M) are control reactions run either in the absence of polymerase (primer only) or in the presence of dNTP substrate for 1 hour at 55° C. (full-length). Panel A shows the activity of selected clones that were tested in the presence of dNTP substrate for 1 hour at 55° C. and in the absence of added substrate for 18 hours at 55° C. to ensure that the recombinant polymerases were properly folded, functional, and free from cellular contaminants. Eight in vitro selected clones were tested for TNA synthesis activity by incubating with tNTPs for 18 hours at 55° C. Panel B shows a time course analysis of TNA synthesis for three engineered polymerase variants in the presence of tNTP substrates.

Figure 10:
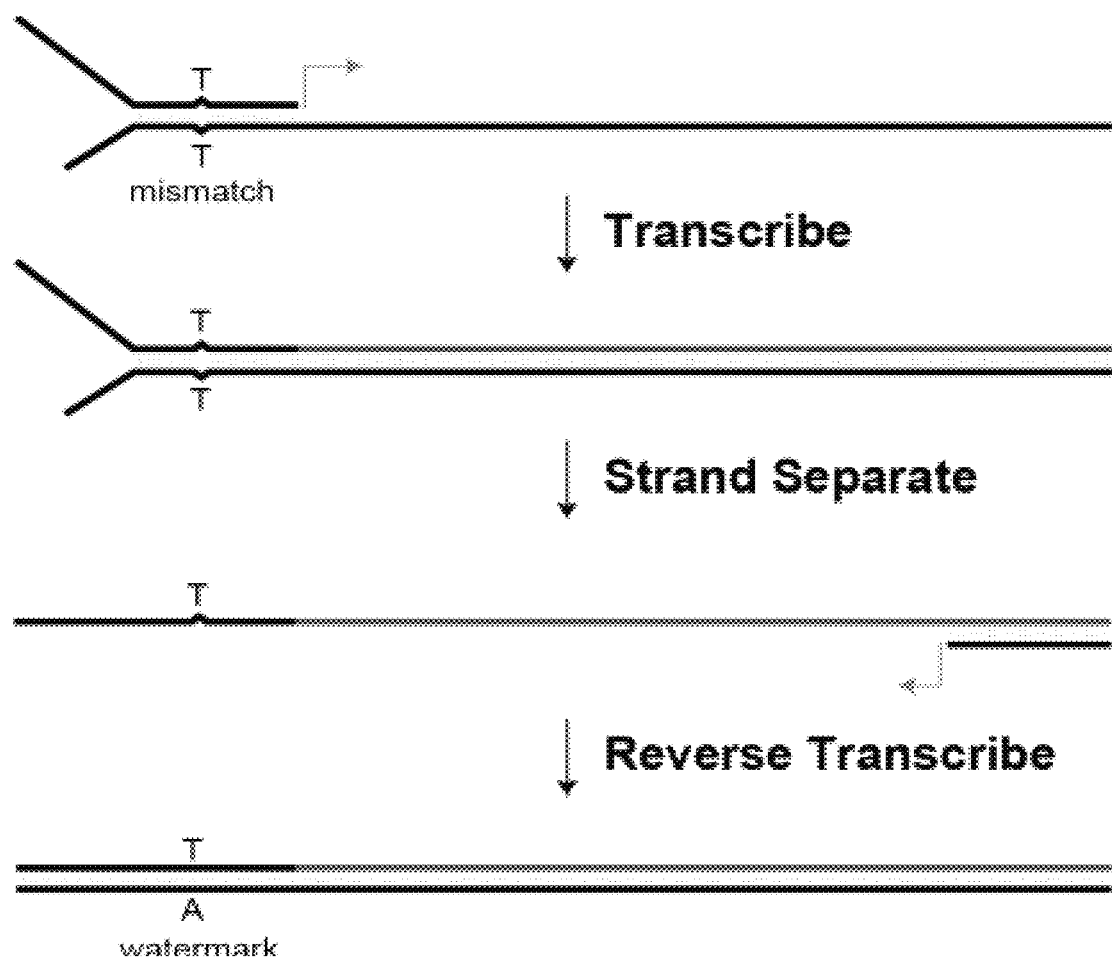

FIG. 10 depicts the replication strategy used to measure TNA fidelity. Schematic representation of the transcription and reverse transcription process used to evaluate the fidelity of TNA replication. DNA is shown in black, TNA is shown in red. The primer-template complex contains a T-T mismatch, which produces a T to A transversion in the cDNA strand. The transversion represents a watermark to ensure that the sequenced DNA was produced by TNA transcription and reverse transcription.

Figure 11:
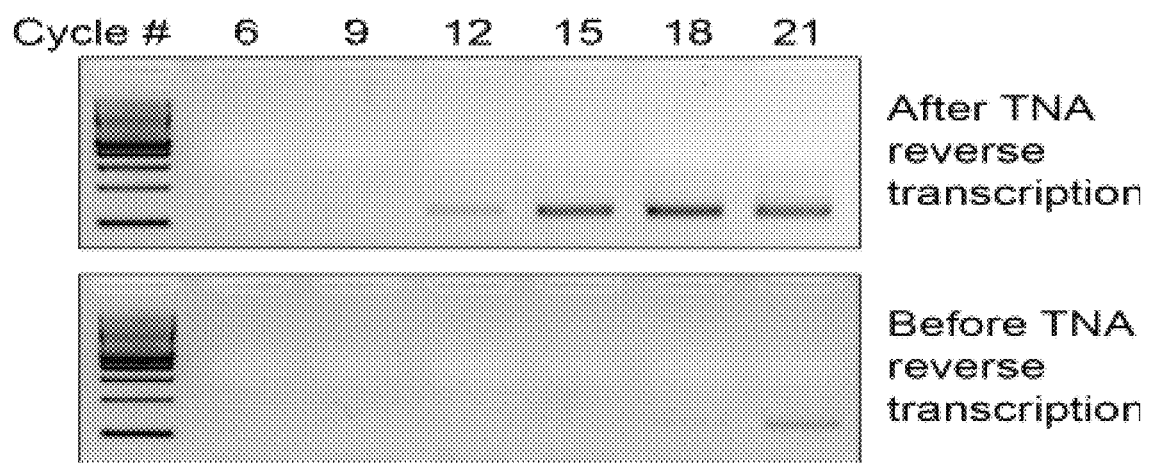

FIG. 11 depicts the control assay for TNA purity. PCR was used to test for DNA contamination prior to TNA reverse transcription (see FIG. 4). DNA amplification before (bottom) and after (top) reverse transcription of the TNA product into cDNA. cDNA amplifies approximately 9 cycles earlier than the contaminating DNA template, representing an ~500-fold excess over background or 99% pure.

DETAILED DESCRIPTION

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

As used herein, the term "xeno-nucleic acid" or "XNA" refers to synthetic alternative to natural nucleic acids DNA and RNA. XNA differs by having a different sugar backbone than the natural nucleic acids. Exemplary XNAs include 1,5-anhydrohexitol nucleic acid (HNA), cyclohexene nucleic acid (CeNA), threose nucleic acid (TNA), glycol nucleic acid (GNA), locked nucleic acid (LNA), and peptide nucleic acid (PNA).

As used herein, the term "the competent cell" refers to a cell modified to take up DNA. An exemplary competent cell for transformation is an *E. coli* cell.

Synthetic genetics aims to develop artificial genetic polymers that can replicate in vitro and eventually in model cellular organisms[4]. Achieving this ambitious goal will require major advances in chemical synthesis and polymerase engineering, as both fields of science are needed to develop the tools necessary for copying information back and forth between DNA and XNA and eventually between XNA polymers themselves. Recognizing that some of the most interesting XNAs can only be obtained by chemical synthesis[7], researchers are facing a pressing need for new synthetic protocols that can be used to generate XNA monomers on the gram scale. Coupled with this effort is the equally challenging demand for new XNA polymerases that can synthesize kilobases of information with no mistakes. While this later goal may seem modest in comparison to natural polymerases, which can faithfully copy a megabase of DNA, the applications envisioned for XNA are less demanding than the biological requirements imposed by cellular organisms[35].

The present invention responds to the need for improved methods of evolving natural DNA polymerase to be a comparably active polymerase for XNA. Evolving enzymes with new or improved function requires iterative rounds of in vitro selection and amplification[13]. The outcome of a selection depends on the number of variants that can be screened and the quality of the separation technique used to partition functional members away from the nonfunctional pool. The miniaturization of directed evolution experiments into artificial compartments with cell-like dimensions provides access to larger enzyme libraries by reducing sample volumes to the picoliter-scale[14, 15]. The simplest approach to water-in-oil (w/o) droplet formation involves the bulk mixing of aqueous and organic phases with vigorous stirring, but this method produces polydisperse droplets with large volumetric differences[14, 15]. Given the cubic dependence of volume on diameter, polydisperse droplets cannot be partitioned by optical sorting due to massive differences in enzyme-substrate concentration[16].

To overcome this problem, microfluidic devices have been developed that can generate monodisperse populations of w/o droplets by manipulating fluids at the microscale[17, 18]. While this approach has been used to change the specificity of several natural enzymes[19-21], this technique has not yet been applied to problems in polymerase engineering due to the challenges of generating a fluorescent signal with a signal-to-noise ration (SNR) that is high enough to distinguish droplets containing functional polymerases from those that are empty or contain nonfunctional enzymes.

The present invention is directed to a microfluidics-based polymerase engineering strategy that combines droplet microfluidics with optical cell sorting. Droplet-based optical polymerase sorting (DrOPS) is a new strategy for engineering polymerases with non-natural functions. The method relies on single and double emulsion droplets that are produced using commercially available microfluidic chips and reagents. The two-chip design simplifies the procedure for generating monodisperse droplets and provides flexibility for controlling such parameters as droplet size and oil-layer thickness[27]. With this system, droplets can be produced and screened in a matter of our hours, which allows a round of selection to take place in 3-4 days. For example, a library of 36 million double emulsion droplets was screened in 2 hours (at 5 kHz) by fluorescence-activated cell sorting. Based on this rate of sorting, it should be possible to screen >$10^8$ droplets per day, which may be necessary for some polymerase functions that require greater library diversity. The strategy functions with high partitioning efficiency, using an optical sensor that could be engineered for other substrate-template combinations.

The DrOPS method has several advantages over existing polymerase engineering technologies. Relative to screening procedures that assay variants in microliter-scale reactions, miniaturization of the PAA into microdroplets reduces the assay volume to the picoliter scale, which is a ~$10^6$-fold reduction in reaction volume per polymerase assay.

This improvement in assay volume size coupled with the ability to sort >$10^8$ droplets per day leads to enormous cost savings for chemically synthesized substrates like tNTPs that require more than 12 synthetic steps to produce[32]. In the case of our 8,000-member library, we performed one round of DrOPS using 200 μL of TNA triphosphate containing reaction buffer, which is equivalent to twenty primer-extension reactions performed under standard bulk-phase conditions. By comparison, traditional screening of the same library with 98% coverage would require 32,000 PAAs and consume >320 milliliters of reaction buffer. This striking difference leads to an economy of scale that benefits microfluidics-based reactions by reducing the consumption of chemically synthesized substrates, which is critical to realizing the long-term of goals of synthetic genetics[4].

DrOPS also compares favorably to other polymerase technologies, like CSR and CST, that use w/o emulsions generated by bulk mixing[1, 12]. While CSR and CST have been used to evolve polymerases with enhanced activity and expanded substrate recognition, both methods use the parent plasmid as template for the primer-extension reaction, which limits the range of polymerase functions to enzymes that promote DNA-templated synthesis. In addition, CST requires affinity purification on a solid-support matrix, which lowers the partitioning efficiency of functional members due to nonspecific DNA binding to the resin. By contrast, DrOPS uses an optical sensor that is amenable to any nucleic acid polymer that is capable of Watson-Crick base pairing and relies on solution-based separation methods, like FACS to separate functional droplets from the nonfunctional pool. Additionally, the ability to specify the sequence composition and length of the template provides enormous control over the stringency of the selection. Together, these properties of template control and solution-based separation make DrOPS a versatile tool that could be applied to a wide range of problems in polymerase engineering.

Although this study examined a specific problem in TNA polymerase engineering, namely, the ability to synthesize TNA in the absence of manganese ions, the DrOPS technology is unique in the sense that it could be applied to other more challenging problems in polymerase engineering. For example, the quantitative aspect of DrOPS could be used to identify new XNA polymerases with superior activity, while the template control aspect provides an avenue for discovering future polymerases that can copy XNA into DNA or possible even XNA into XNA thereby demonstrating direct XNA replication.

Thus, the invention is directed to a microfluidics-based method for evolving novel polymerase functions in vitro. Using DrOPS, a library of polymerase variants is expressed in *E. coli* and single cells are encapsulated in microfluidic droplets containing a fluorescent substrate that is responsive to polymerase activity. Upon lysis, the polymerase is released into the droplet and challenged to extend a primer-template complex with XNA. Polymerases that successfully copy a template strand into full-length product produce a fluorescent signal by disrupting a donor-quencher pair. Although the DrOPS method evolves a manganese-independent TNA polymerase, this technique is usable for evolving any polymerase function where optical detection can be achieved by Watson-Crick base pairing.

Provided are methods of assaying the activity of a target polymerase. The methods comprise expressing the target polymerase in a competent cell and encapsulating the competent cell expressing the target polymerase in a water/oil droplet comprising reagents required for nucleotide synthesis on a DNA primer/template complex. The methods then comprise lysing the competent cell in the water/oil droplet to release the target polymerase; incubating the water/oil droplet to allow the polymerase to assemble nucleoside triphosphates according to the template; emulsifying the water/oil droplet in a bulk aqueous phase to generate a water/oil/water droplet; and detecting the level of fluorescence in the water/oil/water droplet, wherein the level of fluorescence is indicative of the activity of the target polymerase.

Also provided are methods of evolving natural polymerases to accept xeno nucleic acids as substrates. For example, the methods evolve natural polymerase to accept TNA as substrates. The methods comprise expressing a mutated polymerase in a competent cell, wherein the mutated polymerase comprises a mutation in an amino acid residue with a propensity to affect substrate specificity, and encapsulating the competent cell expressing the mutated polymerase in a water/oil droplet. The methods then comprise lysing the competent cell in the water/oil droplet to release the mutated polymerase; incubating the water/oil droplet to allow the mutated polymerase to assemble triphosphates of xeno nucleic acids according to the template; emulsifying the water/oil droplet in a bulk aqueous phase to generate a water/oil/water droplet; and isolating the water/oil/water droplet if the water/oil/water droplet has a level of fluorescence that is at least 10 folds over background. In some implementations, expressing a mutated polymerase in a competent cell comprises generating a mutation in a natural polymerase-encoding DNA sequence that results in a substitution mutation at the amino acid residue with a propensity to affect substrate specificity and introducing the mutated natural polymerase-encoding DNA sequence into the genome of the competent cell.

For both methods of the invention, the encapsulation the competent cell expressing the target polymerase in a water/oil droplet results in the water/oil droplet comprising at most a single competent cell. In some embodiments, methods of evolving natural polymerases to accept xeno nucleic acids as substrates further comprises sorting the water/oil/water droplet by the level of fluorescence prior to isolating water/oil/water droplets. In some implementations, the water/oil/water droplet is sorted using a fluorescence-activated cell sorter.

In some implementations, a hydrophilic microfluidic device is used to emulsify the water/oil droplet in a bulk aqueous phase to generate a water/oil/water droplet. In some embodiments, the hydrophilic microfluidic chip comprises a single inlet flow focusing junction. The geometry of the single inlet flow-focusing junction may be between 3 µm to 200 µm by between 3 µm to 200 µm. For example, the geometry of the single inlet flow focusing junction is 3-20 µm by 3-20 µm, 5-15 µm by 3-20 µm, 3-15 µm by 5-20 µm, 5-15 µm by 5-20 µm, 10-50 µm by 10-50 µm, 25-75 µm by 25-75 µm, 50-100 µm by 50-100 µm, 75-125 µm by 75-125 µm, 100-150 µm by 100-150 µm, 125-175 µm by 125-175 µm, or 150-200 by 150-200 µm. In one embodiment, the geometry of the single inlet flow-focusing junction is 14×17 µm.

In some aspects, introducing the mutated natural polymerase-encoding DNA sequence into the genome of the competent cell comprises transforming the competent cell with a plasmid comprising the mutated natural polymerase-encoding DNA sequence. In some implementations of methods of evolving natural polymerases to accept xeno nucleic acids as substrates, the mutated polymerase originates from *Thermococcus* sp. 9° N. In this embodiment, the amino acid residue with a propensity to affect substrate specificity is selected from the group consisting of: residue 409, residue 485 and residue 664 of the *Thermococcus* sp. 9° N polymerase. In some embodiments of such methods of evolving natural polymerases to accept xeno nucleic acids as substrates, the methods further comprise extracting the plasmid encoding the mutated polymerase from the isolated water/oil/water droplets having a level of fluorescence in the water/oil/water droplet is at least 10 folds over background and transforming a new population of competent cells with the extracted plasmid. The method may further comprise expressing the mutated polymerase encoded by the extracted plasmid and assaying the function of the mutated polymerase with triphosphates of xeno nucleic acids as substrates. For example, where the methods evolve natural polymerase to accept TNA as substrates, the function of the mutated polymerase is assayed with α-L-threofuranosyl nucleic acid triphosphates.

In some implementations of the methods of the invention, a fluorophilic microfluidic chip encapsulates the competent cell expressing the target polymerase or the mutated polymerase in a water/oil droplet. The fluorophilic microfluidic chip comprises a single inlet flow-focusing junction. The geometry of the single inlet flow-focusing junction may be between 3 µm to 200 µm by between 3 µm to 200 µm. For example, the geometry of the single inlet flow focusing junction is 3-20 µm by 3-20 µm, 5-15 µm by 3-20 µm, 3-15 µm by 5-20 µm, 5-15 µm by 5-20 µm, 10-50 µm by 10-50 µm, 25-75 µm by 25-75 µm, 50-100 µm by 50-100 µm, 75-125 µm by 75-125 µm, 100-150 µm by 100-150 µm, 125-175 µm by 125-175 µm, or 150-200 by 150-200 µm. In one embodiment, the geometry of the single inlet flow-focusing junction is 14×17 µm. In some aspects, the fluorophilic microfluidic chip comprises a single inlet flow that is coated with a hydrophobic coating. In some implementations, the water/oil droplet has a diameter of about 0.5 µm, 0.6 µm, 0.7 µm, 0.8, µm, 0.9 µm, 1 µm, 3 µm, 5 µm, 8 µm, 10 µm, 11 m, 12 ti m, 13 ti m, 14 µm, 15 µm, 16 µm, 17 µm, 18 µm, 19 µm, 20 µm, 25 µm, 50 µm, 75 µm, or 100 µm. The water/oil droplet may have a volume of between 1 pL to 30 nL, for example, 1 pL, 5 pL, 10 pL, 25 pL, 30 pL, 1 nL, 5 nL, 10 nL, 15 nL, 20 nL, or 30 nL.

For both methods of the invention, the reagents comprise nucleoside triphosphates and an optical reporter. The optical reporter comprises a primer, a template, a fluorophore, and a quencher. The quencher comprises a modification at the 5' or 3' end. In some implementations, the primer and template is selected form the group consisting of the sequences listed in Table 1.

In some implementations of both methods of the invention, competent cell in the water/oil droplet is lysed by incubation at least 90° C., or preferably at 90° C. In some embodiments, the competent cell in the water/oil droplet is lysed by incubation at at least 90° C. for 5-30 minutes. In other implementations, the competent cell in the water/oil droplet is lysed through chemical means. Chemical means for lysing competent cells are well established in the art, for example, a competent cells may be lysed chemically by a lysis buffer.

In some aspects, incubating the water/oil droplet to allow the polymerase to assemble nucleoside triphosphates according to the template takes place at 37-75° C., for example at 55° to allow the target polymerase or the mutated polymerase to assemble nucleoside triphosphate or triphosphates of xeno nucleic acids according to the template. The duration of this incubation may be between a few minutes to a couple of days depending on the incubation temperature and the polymerase activity. In some implementations of incubating the water/oil droplet to allow the polymerase to assemble nucleoside triphosphates according to the template, the water/oil droplet is incubated at 55° C. for at least 3 hours. In some implementations, the water/oil droplet is incubated at 55° C. for 18 hours.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Elements and acts in the example are intended to illustrate the invention for the sake of simplicity and have not necessarily been rendered according to any particular sequence or embodiment. The example is also intended to establish possession of the invention by the Inventors.

1. Methods a. General Information

DNA oligonucleotides (Table 1) were purchased from Integrated DNA Technologies (Coralville, Iowa), purified by denaturing polyacrylamide gel electrophoresis, electro-eluted, ethanol precipitated, and quantified by UV absorbance using a NanoDrop spectrophotometer. NTPs and dNTPs were purchased from Sigma (St. Louis, Mo.). TNA triphosphates (tNTPs) were obtained by chemical synthesis as previously described[1,2]. Accuprime DNA Polymerase was obtained from Invitrogen (Grand Island, N.Y.). Hen egg lysozyme was purchased from Sigma. Fluorinated oil HFE-7500 was purchased from 3M Novec (St. Paul, Minn.), and microfluidic chips were purchased from Dolomite (UK). The 9n gene was kindly provided by Andreas Marx in a pGDR11 expression vector. DNA sequencing was performed at the ASU Core Facility.

TABLE 1

DNA primer and template sequences.
Modifications are written following IDT nomenclature.
N represents a degenerate position containing an
equal distribution of A, T, G, and C nucleobases.
Engineered primer mismatches are denoted in lowercase.

| Name | DNA Sequence (5' → 3') | SEQ ID NO. |
|---|---|---|
| Lib.409.NNN (DNA template) | GAACGTGAACTGGCGCGCCGTCGTGGCGGTTATGCGGGCGGTTATG TGAAAGAACCGGAACGTGGCCTGTGGGATAACATTGTGTATCTGGA TTTTCGTAGCCTGNNNCCGAGCATTATTATCACCCACAATGTGAGC CCGGATACCCTGAACCGTGAAGGCTGCAAAGAATATGATGTGGCGC CGGAAGTGGGCCATAAATTCTGCAAAGATTTCCCGGGCTTTATT | SEQ ID NO: 1 |
| Lib.485.NNN (DNA template) | AAGATTTCCCGGGCTTTATTCCGAGCCTGCTGGGCGATCTGCTCGA GGAACGCCAGAAAATCAAACGCAAAATGAAAGCGACCGTTGATCCG CTGGAAAAAAAACTGCTGGATTATCGTCAGCGCNNNATTAAAATTC TGGCCAACAGCTTCTATGGCTATTATGGTTATGCGAAAGCGCGTTG GTATTGCAAAGAATGCGCGGAAAGCGTGACCGCGTGGGGCCGTGAA TATATCGAAATGGTGATCCGCGAGCTCGAAGAAAAATTCGGCTTCA AAGTGCTGTATGCGGATACCGATGGCCTGCATGCGACCATTCCGGG TGCGGATGCGGAAACCGTGAAAAAAAAAGCGAAAGAATTCCTGAAA TACATCAATCCGAAACTGCCGGGCCTGCTGGAACTGGAATATGAAG GCTTTTATGTGCGTGGCTTTTTCGTGACCAAAAAAAAATACGCGGT GATCGATGAAGAAGGCAAAATTACCACCCGTGGCCTGGAA | SEQ ID NO: 2 |
| Lib.664.NNN (DNA template) | AATACGCGGTGATCGATGAAGAAGGCAAAATTACCACCCGTGGCCT GGAAATTGTGCGTCGTGATTGGAGCGAAATTGCGAAAGAAACCCAG GCGCGTGTGCTGGAAGCGATTCTGAAACATGGCGATGTGGAAGAAG CGGTGCGTATTGTTAAAGAAGTGACCGAAAAACTGAGCAAATATGA GGTACCGCCGGAAAAACTGGTGATTCATNNNCAAATTACCCGTGAT CTGCGTGATTATAAAGCGACCGGTCCGCATGTGGCGGTGGCAAAAC GTCTGGCAGCGCGTGGCGTGAAAATTCGTCCGGGCACCGTGATTAG CTATATTGTGCTGAAAGGCAGCGGCCGCATTGGCGATCGTGCGATT CCGGCGGATGAATTTGATCCGACCAAACATCGTTATGATGCGGAAT ATTATATCGAAAACCAGGTGCTGCCGGCGGTGGAACGTATTCTGAA AGCGTTTGGCTATCGTAAAGAAGATCTGCGCTATC | SEQ ID NO: 3 |
| P1.For (primer) | AACTGGCGCGCCGTCGTGGCGGTTATGCGG | SEQ ID NO: 4 |
| P1.Rev (primer) | CGTTCCTCGAGCAGATCGCCCAGCAGGCTCGGAATAAAG | SEQ ID NO: 5 |
| P2.For (primer) | ATCTGCTCGAGGAACGCCAGAAAATCAAACGC | SEQ ID NO: 6 |
| P2.Rev (primer) | TTCCAGGCCACGGGTGGTAATTTTGC | SEQ ID NO: 7 |
| P3.For (primer) | AATACGCGGTGATCGATGAAG | SEQ ID NO: 8 |
| P3.Rev (primer) | GATAGCGCAGATCTTCTTTACGATAGCC | SEQ ID NO: 9 |
| PBS2-IR800 (primer) | /5IRD800/GACACTCGTATGCAGTAGCC | SEQ ID NO: 10 |
| ST.1G.Cy3 (DNA template) | /5Cy3/ACAACCATACTCTCCTCATCACTATTCAACTTACAATCGA TACAACCTTATAATCCACATGGCTACTGCATACGAGTGTC | SEQ ID NO: 11 |
| ST.1G.FAM (DNA template) | /56FAM/ACAACCATACTCTCCTCATCACTATTCAACTTACAATCG ATACAACCTTATAATCCACATGGCTACTGCATACGAGTGTC | SEQ ID NO: 12 |
| ST.1G (DNA template) | ACAACCATACTCTCCTCATCACTATTCAACTTACAATCGATACAAC CTTATAATCCACATGGCTACTGCATACGAGTGTC | SEQ ID NO: 13 |
| QP13.Iowa (probe) | AGAGTATGGTTGT/3IABkFQ/ | SEQ ID NO: 14 |
| QP16.Iowa (probe) | AGGAGAGTATGGTTGT/3IABkFQ/ | SEQ ID NO: 15 |
| QP20.Iowa (probe) | GATGAGGAGAGTATGGTTGT/3IABkFQ/ | SEQ ID NO: 16 |
| QP13.BHQ (probe) | AGAGTATGGTTGT/3BHQ_1/ | SEQ ID NO: 17 |
| QP16.BHQ (probe) | AGGAGAGTATGGTTGT/3BHQ_1/ | SEQ ID NO: 18 |

TABLE 1-continued

DNA primer and template sequences.
Modifications are written following IDT nomenclature.
N represents a degenerate position containing an
equal distribution of A, T, G, and C nucleobases.
Engineered primer mismatches are denoted in lowercase.

| Name | DNA Sequence (5' → 3') | SEQ ID NO. |
| --- | --- | --- |
| QP20.BHQ (probe) | GATGAGGAGAGTATGGTTGT/3BHQ_1/ | SEQ ID NO: 19 |
| Fidelity.Temp (DNA template) | TGTCTACACGCAAGCTTACATTAAGACTCGCCATGTTACGATCTGC CAAGTACAGCCTTGAATCGTCACTGGCTACTGCATACGAGTGTC/ 3InvdT/ | SEQ ID NO: 20 |
| PBS2.Mismatch (primer) | CTTTTAAGAACCGGACGAACGACACTCGTtTGCAGTAGCC | SEQ ID NO: 21 |
| PBS1 (primer) | TGTCTACACGCAAGCTTACA | SEQ ID NO: 22 |
| Extra.Primer (primer) | CTTTTAAGAACCGGACGAAC | SEQ ID NO: 23 | b. Generating Emulsion Droplets

All microfluidic devices for monodisperse emulsion formation were purchased from Dolomite, UK based on commercial designs available on their website. Syringe pumps and 1/16" OD fluorinated ethylene propylene (FEP) tubing with 0.01" ID (Idex 1478-20) was used to transport fluids through to microfluidic chips and from the chip outlet to the collection vessels. All fluid connections off chip were formed using 1/16" Upchurch fitting connectors.

The formation of water-in-oil single emulsions was performed using a quartz glass microfluidic device with a single inlet flow focusing junction geometry of 14×17 μm with a hydrophobic/fluorophilic coating (Cat. C000525G, Dolomite, UK). The device was connected by FEP tubing through a top interface linear connector (Cat. 3000109, Dolomite, UK) to syringes [100 μL, 500 μL SGE glass syringes, 2500 μL Hamilton Gastight syringe or 3 mL plastic syringe (Becton-Dickinson, Madrid, Spain)], which were driven by either an NE1002× syringe infusion pumps (New Era Pump Systems Inc., USA) or a pump manifold of neMESYS low pressure syringe pumps (Cetoni Gmbh, Germany) with accompanying control software. Carrier fluid was filtered using a 0.2 μm inline syringe filter, while the aqueous phase was filtered using an inline 10 μm frit filter. Droplet generation was monitored using a Nikon eclipse TS100 microscope with 20× ELWD Nikon objective and captured using a QIclick 12 bit monochrome CCD camera (QImaging, BC Canada). Flow rates were adjusted based on visual inspection with an average rate of 5 μL min-1 for the aqueous phase and 12 μL min-1 for the carrier oil. These flow rates yielded droplets with an average diameter of 14 μm (~1 pL volume). A low viscosity fluorinated oil (HFE-7500, 3M USA) containing 1% (w/w) Pico-Surf surfactant (Dolomite, UK) was used as the carrier fluid.

The formation of w/o/w double emulsions was performed using a quartz glass microfluidic device with a single inlet flow focusing junction geometry of 14×17 μm (Cat. 3200136, Dolomite, UK). The w/o emulsion and aqueous carrier phase were delivered to the device using syringes connected in the same fashion as described above for single emulsion formation. The w/o emulsion was slowly drawn into a 250 μL SGE glass syringe, mounted into an infusion pump in a vertical position and left to settle for at least 30 min prior to delivery. Carrier fluid (25 mM NaCl, 1% Tween-80) was filtered using a 0.2 μm inline syringe filter, while the w/o emulsion was filtered using an inline 10 μm frit filter. Flow rates were adjusted based on visual inspection with an average rate of 1 μL for the single emulsion and 8 μL for the carrier aqueous phase.

c. Cell Compartmentalization in Droplets

Cell populations were grown and polymerase variants were expressed as described herein. After expression, an aliquot (2 mL) of cell culture was centrifuged for 5 min (2,000 rcf) and the supernatant discarded. The cells were washed three times with 1× ThermoPol buffer [20 mM Tris-HCl, 10 mM $(NH_4)_2SO_4$, 10 mM KCl, 2 mM $MgSO_4$, 0.1% Triton X-100, pH 8.8]. After each wash, the cells were centrifuged for 5 min (2,000 rcf) and the supernatant discarded. The rinsed bacterial pellet was re-suspended in 500 μL 1× ThermoPol buffer and the absorbance was measured at 600 nm. Cells were diluted to enable encapsulation at occupancies of 0.1 cells per droplet, according to the assumption that 1 mL of E. coli suspension at an A600 value of 1.0 contains $5\times10^8$ cells. Just prior to emulsification the cells were mixed with the fluorescence-based polymerase activity assay (see section below). The w/o emulsion was collected under a layer of mineral oil in an Eppendorf tube. Following emulsification, the reactions were incubated for 5 min at 90° C. to lyse cells, followed by incubation at 55° C. for the indicated amount of time.

d. Microscopy

Images were collected using a brightfield microscope (Eclipse TE300, Nikon) equipped with a Hamamatsu Orca 3CCD camera using a 60×, 1.32 NA, oil-immersion objective lens and Immersion Oil Type DF (Cargille Laboratories) imaging medium. QED InVivo 3.2 (Media Cybernetics) was used to collect images, which were processed with Photoshop CS4 (Adobe) or ImageJ (NIH) software. Microfluidic droplet generation was monitored using a Nikon eclipse TS100 inverted microscope with either a 10×, 0.3 NA Plan fluor, or 20×, 0.45 NA ELWD S Plan Fluor, Nikon objectives and captured using a QIclick 12 bit monochrome CCD camera (QImaging, BC Canada).

e. Flow Cytometric Analysis of Double Emulsion Droplets w/o/w double emulsion droplets were diluted into 150 mM NaCl and subjected to flow cytometric analysis (FACSCalibur, BD Biosciences). The sample was excited with a 488 nm argon laser and the emission was detected using a 530±15 nm band-pass filter. Double emulsion populations were gated on logFSC/logSSC. Fluorescent readout was obtained from more than 15,000 droplets for each measurement and analyzed using Cytometer software (Cell Quest, BD Biosciences).

f. Polymerase Library Generation

The focused 9n DNA polymerase library was generated by replacing the region coding for the finger, thumb, and palm domains with a DNA cassette containing unbiased, random codons (NNN) at amino acid positions 409, 485, and 664. The DNA cassette was generated from three gBlock fragments that were combined by overlapping PCR using AccuPrime DNA polymerase (FIG. 6). The second fragment contains a 5' region that is conserved with the 3' end of the first fragment and a 3' region that is conserved with the 5' end of the third fragment. Each fragment was individually amplified using three sets of unique primers (P1.For, P1.Rev, P2.For, P2.Rev, P3.For, P3.Rev) with an optimized number of PCR cycles determined by qPCR analysis to prevent over-amplification. The full-length cassette was then assembled by combining 15 ng of each fragment and DNA primers P1.For and P3.Rev into a single PCR reaction. The PCR amplified cassette was digested with AscI and BglII restriction enzymes, ligated into the pGDR11 expression vector, and transformed into electrocompetent 10-beta $E.$ $coli$ (New England Biolabs Inc., Mass., USA).

g. Polymerase Selections

Polymerase variants were grown as a population of $E. coli$ carrying the pGDR11 plasmid encoding the polymerase of interest in Luria-Bertani (LB) broth supplemented with ampicillin (100 μg mL-1). Cultures were grown at 37° C. with shaking at 240 rpm and protein expression was induced by adding IPTG to a final concentration of 1 mM at an OD-600 of 0.6. Induced cultures were grown for an additional 3 hours at 37° C. with shaking. Prior to emulsion formation the cells were washed three times with 1×ThermoPol buffer (NEB) and then diluted to enable encapsulation at occupancies of 0.1 cells per droplet. Just prior to emulsification the cells were mixed with the fluorescence-based polymerase activity assay. The w/o emulsion was collected under a layer of mineral oil in an Eppendorf tube. Following emulsification, the reactions were incubated for 5 min at 90° C. to lyse cells, followed by incubation at 55° C. for the indicated amount of time. Single emulsions were then converted to double emulsions as described above. Prior to sorting droplets using a FACS, the aqueous carrier phase (1% w/w Tween 80 in 25 mM NaCl) was exchanged for a solution of 25 mM NaCl to reduce the presence of surfactant in the aqueous phase. Samples were sorted in a BD FACS Aria (BD Biosciences) using PBS as sheath fluid. A set-up with a 70 μm nozzle was chosen to give an average sort rate of 5,000-8,000 events per second. The threshold trigger was set on side scatter. The sample was excited with a 488 nm argon laser and the emission was detected using a 530 ±15 nm band-pass filter. The double emulsion population was gated from other populations in the sample on logFSC/logSSC. DNA samples were recovered from sorted emulsions by extraction with ~2 volumes of Pico-Break 1 (Dolomite) to disperse the emulsions. The extracted aqueous phase was concentrated using a spin column (Zymo Research) and used to transform electrocompetent $E. coli$ cells (β-10, NEB) Plasmid recovery efficiency was determined by comparing the number of sorted droplets to the number of colonies obtained after transformation and plating.

h. Fluorescence-Activated Droplet Sorting

Prior to sorting droplets using a fluorescence-activated cell sorter (FACS), the aqueous carrier phase (1% w/w Tween 80 in 25 mM NaCl) was exchanged for a solution of 25 mM NaCl to reduce the presence of surfactant in the aqueous phase. Samples were sorted in a BD FACS Aria (BD Biosciences) using PBS as sheath fluid. A set-up with a 70 μm nozzle was chosen to give an average sort rate of 5,000-8,000 events per second. The threshold trigger was set on side scatter. The sample was excited with a 488 nm argon laser and the emission was detected using a 530±15 nm band-pass filter. The double emulsion population was gated from other populations in the sample on logFSC/logSSC.

i. DNA Recovery and Transformation

DNA samples were recovered from sorted emulsions by extraction with ~2 volumes of Pico-Break 1 (Dolomite, UK), which contains 1H,1H,2H,2H-perfluorooctanol (PFO). After addition of Pico-Break 1, the samples were vortexed, followed by centrifugation (15 sec, 2,000 rcf) to attain phase separation. The top, aqueous layer containing the plasmid DNA was recovered. The bottom layer was extracted a second time with one volume of molecular grade water to improve recovery yields. The combined aqueous layers containing the plasmid DNA were concentrated using a spin column (DNA Clean & Concentrator®-5, Zymo Research) and eluted with molecular biology grade water (10 μL). The DNA Clean & Concentrator®-5 also facilitates removal of protein from the sample. Electrocompetent $E. coli$ cells (50 μL, β-10 $E. coli$ cells NEB, USA) were transformed with 5 μL of purified DNA by applying one electric pulse of 1.80 kV (using an $E. coli$ Pulser cuvette, 0.1 cm electrode; Bio-Rad MicroPulser). Sterile S.O.C. Medium (500 μL, Invitrogen) was added immediately after pulsing and the sample was grown for 30 min at 37° C. with shaking at 240 rpm before plating on LB agar containing ampicillin (100 μg mL-1) followed by incubation at 37° C. overnight. Plasmid recovery efficiency was determined by comparing the number of sorted droplets to the number of colonies obtained after transformation and plating. In some cases, dilution plating was used to estimate the number of successful transformants.

j. Polymerase Expression

Individual polymerase variants were tested by growing a clonal population of XL-1 blue $E. coli$ carrying the pGDR11 plasmid encoding the polymerase of interest in LB broth supplemented with ampicillin (100 μg mL$^{-1}$). Cultures were grown at 37° C. with shaking at 240 rpm and protein expression was induced by adding IPTG to a final concentration of 1 mM at an OD-600 of 0.6. Induced cultures were grown for an additional 3 hours at 37° C. with shaking. The cells were then pelleted and re-suspended in nickel binding buffer [50 mM phosphate, 250 mM sodium chloride, 10% glycerol, pH 8] with 0.1 mg mL-1 hen egg lysozyme, and incubated for 1 hour at 37° C. Following lysozyme treatment the samples were heated for 15 minutes at 75° C. Aggregated cellular debris was removed by centrifugation for 15 min at 3,200 rcf. Polymerases were purified from the lysate based on an N-terminal 6× His-tag by binding to a nickel affinity resin. After binding, the resin was washed three times with nickel binding buffer followed by elution with nickel binding buffer supplemented with 75 mM imidazole. Protein expression was confirmed by SDS-PAGE analysis with coomassie blue staining. Polymerases were exchanged into storage buffer [10 mM Tris-HCl, 100 mM KCl, 1 mM DTT, 0.1 mM EDTA, pH 7.4] using a Microcon-30kDa column (Millipore, USA) and stored at 4° C.

k. Polymerase Activity Assays

Polymerase activity was evaluated as the ability to extend a DNA primer-template complex with natural, non-cognate, and unnatural nucleotide triphosphates. Primer-extension reactions were analyzed by denaturing polyacrylamide gel electrophoresis (PAGE) or fluorescence. The primer-template complex was annealed in ThermoPol buffer [1×: 20 mM Tris-HCl, 10 mM $(NH_4)_2SO_4$, 10 mM KCl, 2 mM $MgSO_4$, 0.1% Triton X-100, pH 8.8] (New England Biolabs Inc., Mass., USA) by heating for 5 min at 95° C. and cooling for 5 min at 4° C. Nucleotide triphosphates (100 μM final) and polymerase were added to the reaction after primer annealing and the reaction was incubated at 55° C. for the indicated amount of time.

Fluorescence-based polymerase activity assays were performed using an unlabeled DNA primer, a template with a fluorophore label at the 5' end and a quencher probe labeled with a quencher dye at the 3' end. The concentration of primer, template, and quencher strands were 2, 1 and 3 μM, respectively. Fluorescence was measured using a 2014 EnVision multilabel plate reader (PerkinElmer). For PAGE assays, the DNA primer carried an IR800 fluorophore label at the 5' end and an unlabeled DNA template strand. The concentration of primer and template were 0.5 and 1 μM respectively and no quencher strand was added. Reactions were quenched by adding 10 equivalents of stop buffer [1× Tris-boric acid buffer, 20 mM EDTA, 7 M urea, pH 8]. Samples were denatured for 5 min at 90° C. prior to separation by denaturing PAGE and visualization of the IR800 dye using a LICOR Oddysey CLx imager.

For the polymerase time courses, the reaction volume was increased to 25 μL. At each desired time point, 1 uL of the reaction was removed and added to 30 uL of stop buffer. Samples were then denatured for 5 min at 90° C. prior to separation by denaturing PAGE and visualization of the IR800 dye using a LICOR Oddysey CLx imager. The amount of full length and truncated products were quantified using the Image Studio software version 4.0. All time course assays were completed with the PBS2-IR800 DNA primer and ST.1G DNA template.

1. Fidelity Analysis.

Fidelity reactions were performed by sequencing the cDNA strand following a complete cycle of transcription and reverse-transcription. The primer-template complex was extended in a 100 μL reaction volume containing 100 pmol of fidelity.temp and 100 pmol of PBS2.mismatch primer. The primer and template were annealed in 1×ThermoPol buffer by heating for 5 min at 95° C. and cooling for 10 min at 4° C. The 9n-YRI polymerase (10 μL) was added to the reaction mixture. For TNA extensions in the presence of $Mn^{2+}$, the polymerase was pretreated with 1 mM $MnCl_2$. The reactions were initiated by addition of the TNA nucleotide triphosphates (100 μM). Following a 4-hour incubation with $Mn^{2+}$ or an 18-hour incubation without $Mn^{2+}$ at 55° C., the reactions were quenched in stop buffer and denatured at 90° C. for 5 min. Elongated primers were purified by denaturing PAGE, electroeluted, and concentrated using a YM-30 concentrator device.

The purified transcripts were reverse transcribed in a final volume of 100 μL. PBS1 primer (100 pmol) was annealed to the template in 1× First Strand Buffer [50 mM Tris-HCl, 75 mM KCl, 3 mM $MgCl_2$, pH 8.3] by heating for 5 min at 90° C. and cooling for 10 min at 4° C. Next, 500 μM dNTPs and 10 mM DTT was added and the reaction was allowed to incubate for 2 min at 42° C. Finally, 3 mM $MgCl_2$, 1.5 mM $MnCl_2$, and 10 U $μL^{-1}$ SuperScript II reverse transcriptase were added and the reaction was allowed to incubate for 1 hour at 42° C.

After reverse transcription, the PCR amplified DNA (1 pmol) was ligated into a pJET vector following manufacturer's protocol. The ligated product was transformed into XL1-blue E. coli, grown in liquid media, and individual colonies were isolated, cloned, and sequenced (ASU Core Facility). Sequencing results were analyzed using CLC Main Workbench. Sequences lacking the T to A watermark were discarded as they were generated from the starting DNA template rather than replicated material. The error rate for each of the nine possible substitution (for example T→C, T→G, or T→A) was determined as follows: μ exp.→obs= (#observed/#expected)*1000. The total error rate was determined by summing the error rate for each substitution.

2. Results a. Fluorescence-Based Polymerase Activity Assay

Figure 1:
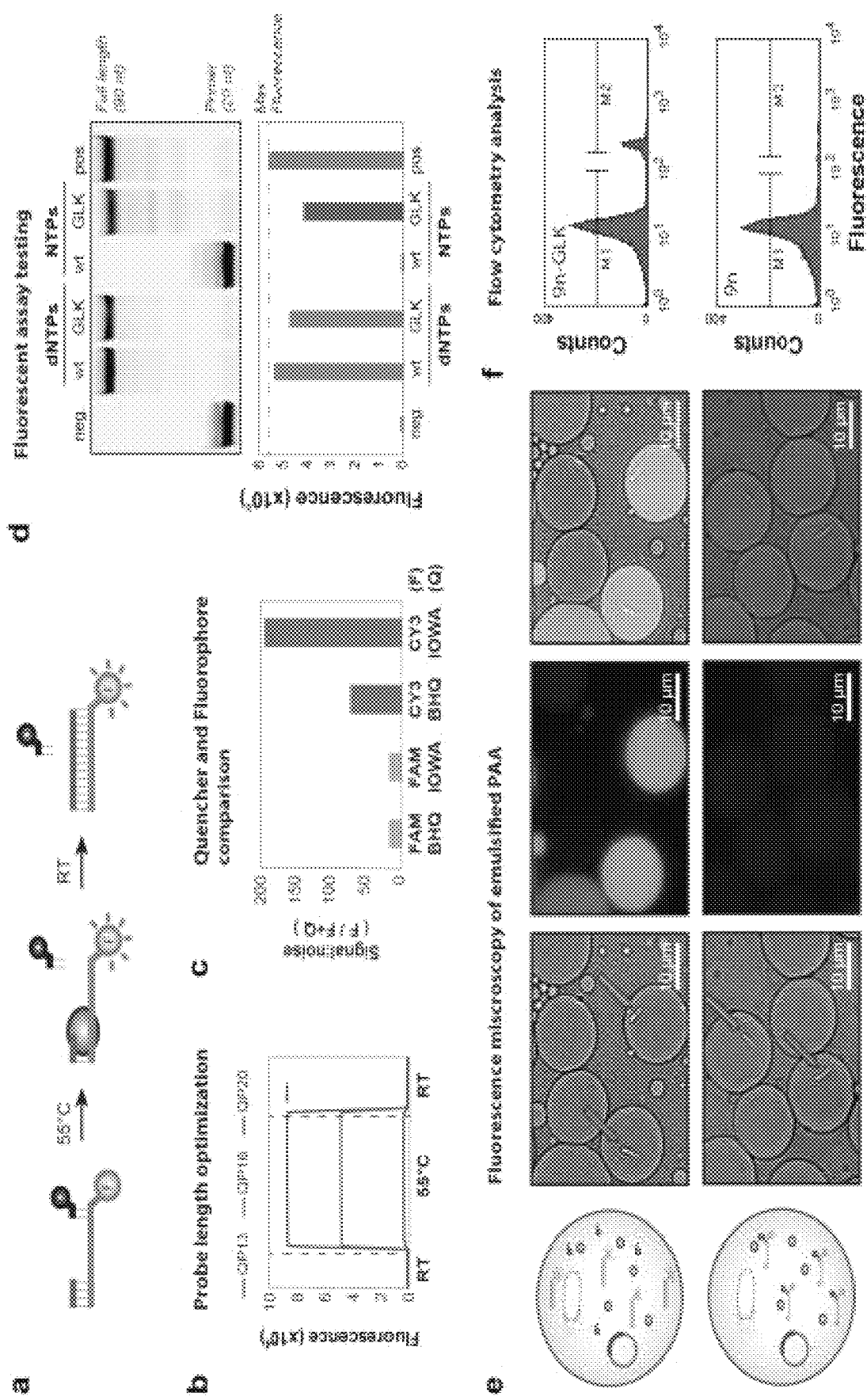
FIG. 1 depicts the process of droplet-based optical polymerase sorting (DrOPS). Panel A shows a fluorescent reporter system that produces an optical signal when a primer-template complex is extended to full-length product. The reporter consists of a primer-template complex (pink and green) containing a downstream fluorophore that is quenched when a DNA-quencher (black) anneals to the unextended region. Panel B depicts optimization of the probe length. The assay was designed with a metastable probe to allow dissociation at elevated temperatures where thermophilic polymerases function with optimal activity. Red arrow marks the maximum fluorescence observed in the absence of the quencher-probe. Panel C depicts screening of fluorophore (F)/quencher (Q) pairs were screened to identify a dye pair with the maximum signal-to-noise ratio. Panel D analyses primer-extension by denaturing PAGE (top) and fluorescence (bottom) for 9n and 9n-GLK polymerases using dNTP and NTP substrates.

Molecular beacons previously developed to monitor polymerase function suffer from a low SNR that precludes their use in w/o droplets[22, 23]. We therefore set out to design a polymerase activity assay (PAA) that would produce a strong optical signal when a primer-template complex is extended to full-length product, but remain dim when the primer goes unextended (FIG. 1 Panel A). With this goal in mind, a DNA quencher-probe was designed to dissociate from the primer-template complex at elevated temperatures where thermophilic polymerases function with optimal activity and re-anneal at room temperature when the sample is assayed for function (FIG. 1 Panel B). By coupling polymerase activity to fluorescence, genes encoding functional polymerases are identified by the optical signal of their droplet, while variants that fail to extend the primer remain dim and are removed from the pool during cell sorting.

Recent advances in the chemistry of dark quenchers caused us to speculate that a donor-quencher pair could be identified with improved spectral properties[24]. By surveying a small number of fluorescent dyes, we found that Cy3 produces an optical signal that is 200-fold higher than its quenched state with Iowa Black® RQ (FIG. 1 Panel C), which is substantially higher than previous donor-quencher pairs developed to monitor polymerase activity[22].

To test the Cy3-Iowa Black® RQ donor-quencher pair in a PAA, the RNA synthesis activity of an engineered DNA polymerase was compared to its wild type (wt) DNA polymerase counterpart. For this experiment, we used 9n-GLK, which is an engineered version of a DNA polymerase isolated from Thermococcus sp. 9° N that carries the mutations Y409G, A485L, and E664K25. Exonuclease deficient versions of 9n-GLK and wt 9n were challenged to extend a DNA primer-template complex with deoxyribonucleoside triphosphates (dNTP) and ribonucleoside triphosphates (NTP). Analysis of the primer-extension reactions by denaturing polyacrylamide gel electrophoresis (PAGE) and fluorescence confirmed that full-length product is obtained in all cases except when the wt polymerase is incubated with NTPs (FIG. 1 Panel D). This result is consistent with the strong steric gate activity of natural DNA polymerases[26]. More importantly, however, the strong concordance observed between the PAGE and fluorescence-analyzed data (FIG. 1 Panel D) demonstrates that the Cy3-Iowa Black® RQ donor-quencher produces an optical signal suitable for monitoring polymerases activity in a bulk aqueous environment.

b. Miniaturizing the Polymerase Activity Assay

Next, we sought to miniaturize the PAA by encapsulating the primer-template complex in uniform w/o droplets. We began by making w/o droplets in a flow-focusing, fluorocarbon-coated microfluidic device (FIG. 4). In this system, droplet formation occurs at the flow-focusing junction where the aqueous phase meets a fluorous oil carrier phase. The droplets are stabilized by surfactants in the oil that prevent coalescence at elevated temperatures (as high as 90° C.) and allow for long-term storage at room temperature.

To demonstrate that the PAA functions within the environment of a w/o droplet, strains of *E. coli* expressing the wt and 9n-GLK mutant polymerases were encapsulated with the reagents needed for RNA synthesis on a DNA primer-template complex. Droplets were formed following a Poisson distribution ($\mu$=0.1) to ensure that 99% of the occupied droplets contain at most a single *E. coli* cell. This prediction was empirically validated using cells expressing the GFP (FIG. 5). Once formed, the droplets were heated to promote *E. coli* lysis and incubated for 3 hours at 55° C. to facilitate primer extension. Fluorescence and bright field images were taken to assess polymerase activity in a population of w/o droplets. As shown in FIG. 1 Panel E, droplets containing the 9n-GLK *E. coli* strain produce a highly fluorescent signal due to the strong RNA synthesis activity of 9n-GLK, while empty droplets or droplets that contain the wild type 9n *E. coli* strain remain dim. Taken together, these images demonstrate that the PAA functions with high activity in uniform w/o compartments, which is a necessary criterion for developing a microfluidics-based method for polymerase evolution.

c. Formation of Double Emulsion Droplets

While w/o droplets provide a physical barrier for maintaining the genotype-phenotype linkage of functional enzymes, the organic carrier phase poses an obstacle for isolating fluorescent droplets using a commercial FACS. This problem can be overcome by performing a second compartmentalization step in which w/o droplets are emulsified in w/o/w double-emulsion droplets that have an aqueous carrier phase[27]. We therefore prepared a set of double emulsion compartments using a hydrophilic microfluidics device that combines the w/o droplets with an aqueous carrier phase at the flow-focusing junction (FIG. 4). Two populations of single emulsion droplets containing either 9n-GLK or wt 9n DNA polymerase were converted to w/o/w droplets and analyzed by flow cytometry (FIG. 1 Panel F). The population generated with *E. coli* cells expressing the wt 9n polymerase display uniformly low fluorescence, while droplets generated with *E. coli* cells expressing 9n-GLK have a bimodal distribution with low and high fluorescence. The fraction of highly fluorescent droplets correlates with the expected bacterial occupancy of ~10% as predicted by statistical analysis and the GFP encapsulation assay (FIG. 5). Moreover, the difference in average fluorescence intensity between the two populations is greater than 10-fold, which is sufficient to separate the two populations by FACS.

d. Enrichment Efficiency

To test the ability of the PAA to support a complete round of in vitro selection (FIG. 2 Panel A, FIG. 6), we performed a mock selection to measure the amount of enrichment that occurs per round of selection using the DrOPS method. *E. coli* cells expressing the 9n wt polymerase were combined with 1/100th, 1/1,000th, and 1/10,000th of one equivalent of *E. coli* cells expressing 9n-GLK as a positive control for RNA synthesis activity. The 9n-GLK plasmids were engineered to contain a unique NotI restriction site to distinguish 9n-GLK from wt-9n in a restriction enzyme digestion (FIG. 2 Panel B). Accordingly, the three populations of *E. coli* were encapsulated in w/o droplets at an occupancy level of ~10%, which ensured that 99% of the occupied droplets contained no more than one *E. coli* per compartment. Following cell lysis and primer extension, the samples were passed through a second microfluidics device to generate three populations of w/o/w droplets that were each sorted by FACS (FIG. 4). Plasmid DNA recovered from the different populations was amplified by PCR and digested with NotI restriction enzyme. Comparison of the digested DNA before and after sorting revealed an enrichment of 1,200-fold of 9n-GLK (FIG. 2 Panels B and C), which is consistent with previous literature results where model libraries have been sorted in w/o/w double emulsion droplets[27].

e. Evolving a Manganese-Independent TNA Polymerase

Evolving a polymerase that could synthesize an artificial genetic polymer with a backbone structure unrelated to natural DNA and RNA is an exemplary practical application of the DrOPs technology. For this experiment, we chose $\alpha$-L-threofuranosyl nucleic acid (TNA)—an unnatural genetic polymer composed of repeating units of $\alpha$-L-threofuranosyl sugars linked by 2',3'-phosphodiester bonds (FIG. 3 Panel A)[28]. TNA is an attractive candidate for therapeutic and diagnostic applications due to its stability against nuclease degradation and ability to undergo Darwinian evolution[3]. However, the current generation of TNA polymerases suffers from low fidelity due to a propensity for G-G mispairing in the enzyme active site[29].

We hypothesized that the low fidelity of TNA synthesis was due to the presence of manganese ions ($Mn^{2+}$), which are used to relax the substrate specificity of natural polymerases[30]. We therefore designed an in vitro selection strategy to evolve a $Mn^{2+}$-independent TNA polymerase in hopes of generating an enzyme that functions with higher fidelity. A polymerase library was constructed in which positions 409, 485, and 664 in the 9n DNA polymerase scaffold were fully saturated with all possible amino acid mutations. These positions were chosen based on their known propensity to alter the substrate specificity of natural polymerases[31]. The 8,000-member library was assembled from commercial gene blocks (FIG. 7), cloned into *E. coli* and sequence verified. Because the sequencing results revealed a number of random mutations in the gene-coding region, including unwanted stop codons, a single round of selection was performed under standard DNA synthesis conditions to increase the proportion of active clones. SDS-PAGE analysis of randomly selected clones before and after active polymerase enrichment revealed a dramatic increase in the number of full-length enzymes, indicating that neutral selection removed the truncated nonfunctional polymerases from the pool (FIG. 8).

Next, the plasmid library was taken through a complete round of in vitro selection and amplification (FIG. 6). Following w/o droplet formation and *E. coli* lysis, the polymerases were challenged to extend a DNA primer-template complex with chemically synthesized TNA triphosphates (tNTPs) in manganese-deficient reaction buffer for 18 hours at 55° C.[32, 33]. The w/o droplets were converted to double emulsions and sorted by FACS. Plasmid DNA was extracted, transformed into a new population of *E. coli* and library members were cloned and sequenced.

f. Characterizing Selected TNA Polymerases

Eight polymerase variants were chosen for functional analysis (FIG. 3 Panel B). Each polymerase was purified by affinity chromatography, quantified, and assayed for the ability to extend a DNA primer-template complex with chemically synthesized tNTPs. Control experiments performed in the presence and absence of dNTP substrate confirmed that each polymerase was functional and free of cellular contaminants that could lead to a false positive result in the PAA (FIG. 9). Of the 8 polymerases tested, 2 variants showed a significant propensity for TNA synthesis in the absence of manganese ions (FIG. 3 Panel B).

Clone 1 (9n-YRI) carries the mutations A485R and E6641 and retains the wt tyrosine residue (Y) at position 409. Clone 6 (9n-NVA) carries the mutations Y409N, A485V, and E664A as well as two additional point mutations (D432G and V636A). A time course analysis comparing 9n-YRI and 9n-NVA to wt 9n (FIG. 3c) indicates that both engineered polymerases function as strong $Mn^{2+}$-independent TNA polymerases, generating ~50% full-length product in 3 and 9 hours, respectively. By contrast, wt 9n shows very little full-length product after 18 hours of incubation under identical conditions (FIG. 3 Panel C, FIG. 9), indicating that the selected mutations enable 9n DNA polymerase to synthesize TNA in the absence of manganese ions.

g. TNA Replication Fidelity

The strong TNA synthesis efficiency of 9n-YRI provided an opportunity to compare the effect of manganese ions on the fidelity of TNA synthesis. The fidelity of TNA synthesis was analyzed by sequencing more than 2,000 nucleotide positions isolated from the cDNA product generated after a complete cycle of TNA replication (DNA→TNA→DNA) (FIG. 10). Unlike kinetic fidelity assays which examine a single nucleotide insertion event[34], DNA sequencing provides a more complete view of the replication cycle by identifying insertions, deletions, and mutations that occur when genetic information is converted from DNA into TNA and then in a separate reaction from TNA back into DNA'.

A series of controls were used to ensure that the sequencing data reflected the accuracy of TNA 'transcription' and 'reverse transcription' in the primer-extension reactions. The first control was a PCR assay that tested for DNA contaminants in the TNA product isolated by PAGE purification (FIG. 11). In no cases did we observe a PCR product that amplified with the same number of cycles as the cDNA strand isolated from the reverse transcription of a TNA template into DNA. The second control involved checking the sequencing product to ensure that a T to A mutation occurred in the primer-binding site. The TNA synthesis reaction was performed with a primer that contained a single-nucleotide mismatch that would lead to a T to A mutation when the TNA strand was reverse transcribed into DNA but be lacking in sequences that were amplified from DNA contaminants[3] (Table 2).

TABLE 2

DNA sequencing results from aggregate fidelity assay performed in the absence of $Mn^{2+}$. PBS2.mismatch and PBS1 primer sites are underlined. Control watermark (bolded) confirmed the cDNA read underwent TNA replication (see FIG. 10).

| | | |
|---|---|---|
| Read 1 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 24 |
| Read 2 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 25 |
| Read 3 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 26 |
| Read 4 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 27 |
| Read 5 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 28 |
| Read 6 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 29 |
| Read 7 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 30 |
| Read 8 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 31 |
| Read 9 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 32 |
| Read 10 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 33 |
| Read 11 | CTTTTAAGAACCGGACGAACGACACTCGTTTGCAGTAGCCCCATTCTTCAACAGC<br>TCATCACTAGACATTTATAAGTCAACATTAACCTCTGTCTACACGCAAGCTTACA | SEQ ID NO: 34 |
| Read 12 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 35 |
| Read 13 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 36 |
| Read 14 | CTTTTAAGAACCGGACGAACGACACTCGTTTGCAGTAGCCCCATTCTTTAACAGC<br>TCATCACTAGACATTTATAAGTCAACATTAATCTCTGTCTACACGCAAGCTTACA | SEQ ID NO: 37 |
| Read 15 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 38 |
| Read 16 | CTTTTAAGAACCGGACGAACGACACTCGTTTGCAGTAGCCCCATTCTTTAACAGC<br>TCATCACTAGACATTTACAAGTCAACATTAACCTCTGTCTACACGCAAGCTTACA | SEQ ID NO: 39 |

TABLE 2-continued

DNA sequencing results from aggregate fidelity assay performed in the absence of $Mn^{2+}$. PBS2.mismatch and PBS1 primer sites are underlined. Control watermark (bolded) confirmed the cDNA read underwent TNA replication (see FIG. 10).

| | | |
|---|---|---|
| Read 17 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 40 |
| Read 18 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 41 |
| Read 19 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 42 |
| Read 20 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 43 |
| Read 21 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 44 |
| Read 22 | CTTTTAAGAACCGGACGAACGACACTCGTTTGCAGTAGCCCCATTCTTTAACAGC<br>TCATCACTAGACATTTATAAGTCAACATTAACCCCTGTCTACACGCAAGCTTACA | SEQ ID NO: 45 |
| Read 23 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 46 |
| Read 24 | CTTTTAAGAACCGGACGAACGACACTCGTTTGCAGTAGCCCCATTCTTTAACAGC<br>TCATCACTAGACATTTATAAGTCAACATTAACCTCTGTCTACACGCAAGCTTACA | SEQ ID NO: 47 |
| Read 25 | CTTTTAAGAACCGGACGAACGACACTCGTTTGCAGTAGCCCCATTCTTTAACAGC<br>TCATCACTAGACATTTATAAGTCAACAATAACCTCTGTCTACACGCAAGCTTACA | SEQ ID NO: 48 |

Analysis of the sequencing results indicates that a TNA replication cycle performed with 9n-YRI as the TNA polymerase and superscript II as the reverse transcriptase produces ~2 mistakes out of 1,000 nucleotide incorporations when manganese ions are absent from the TNA synthesis reaction. By contrast, the mutation rate is ~50-fold higher when the same reaction performed in the presence of manganese ions (FIG. 3 Panel D). This striking result confirms the hypothesis that manganese ions lower the fidelity of TNA synthesis and provides a viable strategy for faithful TNA synthesis under conditions that more closely approximate natural DNA synthesis. In this regard, 9n-YRI and 9n-NVA, represent the first demonstration of TNA polymerases that functions in the absence $Mn^{2+}$ (FIG. 3 Panel C and FIG. 9 Panel B).

REFERENCES

1. Pinheiro, V. B. et al. Synthetic genetic polymers capable of heredity and evolution. Science 336, 341-344 (2012).

2. Yu, H., Zhang, S. & Chaput, J. C. Darwinian evolution of an alternative genetic system provides support for TNA as an RNA progenitor. Nat. Chem. 4, 183-187 (2012).

3. Yu, H., Zhang, S., Dunn, M. & Chaput, J. C. An efficient and faithful in vitro replication system for threose nucleic acid. J. Am. Chem. Soc. 135, 3583-3591 (2013).

4. Chaput, J. C., Yu, H. & Zhang, S. The emerging world of synthetic genetics. Chem. Biol. 19, 1360-1371 (2012).

5. Pinheiro, V. B., Loakes, D. & Holliger, P. Synthetic polymers and their potential as genetic materials. Bioessays 35, 113-122 (2012).

6. Joyce, G. F. Toward an alternative biology. Science 336, 307-308 (2012).

7. Anosova, I. et al. The structural diversity of artificial genetic polymers. Nucleic Acids Res. doi: 10.1093/nar/gkv1472 (2016).

8. Horhota, A. et al. Kinetic analysis of an efficient DNA-dependent TNA polymerase. J. Am. Chem. Soc. 127, 7427-7434 (2005).

9. Kempeneers, V., Vastmans, K., Rozenski, J. & Herdewijn, P. Recognition of threosyl nucleotides by DNA and RNA polymerases. Nucleic Acids Res. 31, 6221-6226 (2003).

10. Loakes, D. & Holliger, P. Polymerase engineering: towards the encoded synthesis of unnatural polymers. Chem. Commun., 4619-4631 (2009). 11. Chen, T. & Romesberg, F. E. Directed polymerase evolution. FEBS Lett. 588, 219-229 (2014).

12. Ghadessy, F. J., Ong, J. L. & Holliger, P. Directed evolution of polymerase function by compartmentalized self-replication. Proc. Natl. Acad. Sci. USA 98, 4552-4557 (2001).

13. Turner, N.J. Directed evolution drives the next generation of biocatalysts. Nat. Chem. Biol. 5, 567-573 (2009).

14. Griffiths, A. D. & Tawfik, D. S. Man-made enzymes—from design to in vitro compartmentalization Curr. Opin. Biotech. 11, 338-353 (2000).

15. Tawfik, D. S. & Griffiths, A. D. Man-made cell-like compartments for molecular evolution. Nat. Biotechnol. 16, 652-656 (1998).

16. Kaltenbach, M., Devenish, S. R. & Hollfelder, F. A simple method to evaluate the biochemical compatability of oil/surfactant mixtures for experiments in microdroplets. LabChip 12, 4185-4192 (2012).

17. Anna, S. L., Bontoux, N. & Stone, H. A. Formation of dispersions using "flow focusing" in microchannels. Appl. Phys. Lett. 82, 364-366 (2003).

18. Umbanhowar, P. B., Prasad, V. & Weitz, D. A. Monodisperse emulsion generation via drop break off in a coflowing stream. Langmuir 16, 347-351 (2000).

19. Agresti, J. J. et al. Ultrahigh-throughput screening in drop-based microfluidics for directed evolution. Proc. Natl. Acad. Sci. USA 107, 4004-4009 (2010).

20. Sjostrom, S. L. et al. High-throughput screening for industrial enzyme production hosts by droplet microfluidics. Lab Chip 14, 806-813 (2014).

21. Fischlechner, M. et al. Evolution of enzyme catalysts caged in biomimetic gel-shell beads. Nat. Chem. 6, 791-796 (2014).

22. Summerer, D. & Marx, A. A molecular beacon for quantitative monitoring of the DNA polymerase reaction in real-time. Angew. Chem. Int. Ed. 31, 3620-3622 (2002).

23. Dorjsuren, D. et al. A real-time fluorescence method for enzymatic characterization of specialized humn DNA polymerases. Nucleic Acids Res. 37, e128 (2009).

24. Marras, S. Selection of fluorophore and quencher pairs for fluorescent nucleic acid hybridization probes. Methods Mol Biol 335, 3-16 (2006).

25. Dunn, M. R., Otto, C., Fenton, K. E. & Chaput, J. C. Improving polymerase activity with unnatural substrates by sampling mutations in homologous protein architectures. ACS Chem. Biol. 10.1021/acschembio.5b00949 (2016).

26. Brown, J. A. & Suo, Z. Unlocking the sugar "steric gate" of DNA polymerases. Biochemicstry 50, 1135-1142 (2011).

27. Zinchenko, A. et al. One in a million: flow cytometric sorting of single cell-lysate assays in monodisperse picoliter double emulsion droplets for directed evolution. Anal. Chem. 86, 2526-2533 (2014).

28. Schoning, K. U. et al. Chemical etiology of nucleic acid structure: the alpha-threofuranosyl-(3'→') oligonucleotide system. Science 290, 1347-1351 (2000).

29. Dunn, M. R. et al. Terminator-mediated synthesis of unbiased TNA polymers requires 7-deazaguanine to suppress G-G mispairing during TNA transcription. J. Am. Chem. Soc. 137, 4014-4017 (2015).

30. Tabor, S. & Richardson, C. C. Effect of manganese ions on the incorporation of dideoxynucleotides by bacteriophage T7 DNA polymerase and *Escherichia coli* DNA polymerase I Proc. Natl. Acad. Sci. USA 86, 4076-4080 (1989).

31. Cozens, C., Pinheiro, V. B., Vaisman, A., Woodgate, R. & Holliger, P. A short adaptive path from DNA to RNA polymerases. Proc. Natl. Acad. Sci. USA 109, 8067-8072 (2012).

32. Sau, S. P., Fahmi, N. E., Liao, J.-Y., Bala, S. & Chaput, J. C. A scalable synthesis of α-L-threose nucleic acid monomers. J. Org. Chem. 10.1021/acs.joc.5b02768 (2016).

33. Zhang, S., Yu, H. & Chaput, J. C. Synthesis of threose nucleic acid (TNA) triphosphates and oligonucleotides by polymerase-mediated primer extension. Curr. Protoc. Nucleic Acid Chem. 52, 4.54 (2013).

34. Goodman, M. F., Creighton, S., Bloom, L. B. & Petruska, J. Biochemical basis of DNA replication fidelity. Crit. Rev. Biochem. Mol. Biol. 28, 83-126 (1993).

35. Steitz, T. A. DNA polymerases: structural diversity and common mechanisms. J. Biol. Chem. 274, 17395-17398 (1999).

36. Romero, P. A., Tran, T. M. & Abate, A. R. Dissecting enzyme function with microfluidic-based deep mutational scanning. Proc. Natl. Acad. Sci. USA 112, 7159-7164 (2015).

---

The invention claimed is:

1. A method of screening for polymerases that accept xeno nucleic acids as substrates, the method comprising:
   expressing mutated polymerases in competent cells, wherein the mutated polymerase comprises a mutation in an amino acid residue with a propensity to affect substrate specificity and each competent cell is transformed to express one unique mutant polymerase;
   encapsulating the competent cell expressing the mutated polymerase in a water/oil droplet via a fluorophilic microfluidic chip, wherein:
   the water/oil droplets have a diameter selected from the group consisting of: 5 µm, 8 µm, 10 µm, 11 µm, 12 µM, 13 µM, 14 µM, 15 µM, 16 µM, 17 µM, 18 µM, and 19 µm, or a volume of 1 pL or 5 pL;
   a single water/oil droplet comprises at most a single competent cell and the water phase of the water/oil droplet comprises reagents required for nucleotide synthesis on a DNA primer/template complex, the reagents comprising triphosphates of xeno nucleic acids and an optical reporter, the optical reporter comprising
   the DNA primer/template complex, wherein the DNA primer/template complex comprises a primer and a DNA template;
   a fluorophore, and
   a quencher, wherein the quencher comprises a modification at the 5' or 3' end;
   lysing the competent cell in the water/oil droplet to release the mutated polymerase; and
   incubating the water/oil droplet to allow the mutated polymerase to assemble triphosphates of xeno nucleic acids according to the DNA template.

2. The method of claim 1, wherein expressing mutated polymerases in competent cells comprises generating a mutation in a natural polymerase-encoding DNA sequence that results in a substitution mutation at the amino acid residue with a propensity to affect substrate specificity and transforming the competent cell with a plasmid comprising the mutated natural polymerase-encoding DNA sequence.

3. The method of claim 1, wherein the mutated polymerase originates from *Thermococcus* sp. 9° N, the amino acid residue with a propensity to affect substrate specificity is selected from the group consisting of residue 409, residue 485 and residue 664.

4. The method of claim 1, wherein the triphosphates of xeno nucleic acids are α-L-threofuranosyl nucleic acid triphosphates.

5. The method of claim 1, wherein the fluorophore is Cy3 and is coupled to the downstream end of the template and the quencher is Iowa Black® RQ and is coupled to the primer.

6. The method of claim 1, wherein the competent cell is *E. coli*.

7. The method of claim 1, wherein the fluorophilic microfluidic chip comprises a single inlet flow focusing junction geometry of 14×17 μm.

8. The method of claim 1, wherein the fluorophilic microfluidic chip comprises a single inlet flow that is coated with a hydrophobic coating.

9. The method of claim 1, wherein the water/oil droplet have a diameter of about 14 μm or a volume of 1 pL.

10. The method of claim 1, wherein the competent cell in the water/oil droplet is lysed by incubation at 90° C.

11. The method of claim 10, wherein the competent cell in the water/oil droplet is lysed by incubation at 90° C. for 5 minutes.

12. The method of claim 1, wherein the water/oil droplet is incubated at 55° C. to allow the target polymerase or the mutated polymerase to assemble nucleoside triphosphate or triphosphates of xeno nucleic acids according to the template.

13. The method of claim 12, wherein the water/oil droplet is incubated at 55° C. for at least 3 hours.

14. The method of claim 12, wherein the water/oil droplet is incubated at 55° C. for 18 hours.

15. The method of claim 1, further comprising:
emulsifying the water/oil droplet in a bulk aqueous phase to generate a water/oil/water droplet; and
isolating the water/oil/water droplet if the water/oil/water droplet has a level of fluorescence that is at least 10 folds over background.

16. The method of claim 15, further comprising sorting the water/oil/water droplet by the level of fluorescence prior to isolating water/oil/water droplets.

17. The method of claim 16, wherein the water/oil/water droplet is sorted using a fluorescence-activated cell sorter.

18. The method of claim 15, wherein expressing mutated polymerases in competent cells comprises generating a mutation in a natural polymerase-encoding DNA sequence that results in a substitution mutation at the amino acid residue with a propensity to affect substrate specificity and transforming the competent cell with a plasmid comprising the mutated natural polymerase-encoding DNA sequence, the method further comprises:
extracting the plasmids encoding the mutated polymerase from the isolated water/oil/water droplets having a level of fluorescence in the water/oil/water droplet is at least 10 folds over background; and
transforming a new population of competent cells with the extracted plasmids.

19. The method of claim 18, further comprising expressing the mutated polymerase encoded by the extracted plasmid; and assaying the function of the mutated polymerase with triphosphates of xeno nucleic acids as substrates.

20. The method of claim 15, wherein the water/oil droplet in a bulk aqueous phase to generate a water/oil/water droplet is emulsified using a hydrophilic microfluidic device.

* * * * *

SEQUENCE LISTING

```
<160> NUMBER OF SEQ ID NOS: 48

<210> SEQ ID NO 1
<211> LENGTH: 228
<212> TYPE: DNA
<213> ORGANISM: Artificial Sequence
<220> FEATURE:
<223> OTHER INFORMATION: DNA template
<220> FEATURE:
<221> NAME/KEY: misc_feature
<222> LOCATION: (106)..(108)
<223> OTHER INFORMATION: n represents a degenerate position containing
      an equal distribution of A, T, G, and C nucleobases

<400> SEQUENCE: 1
gaacgtgaac tggcgcgccg tcgtggcggt tatgcgggcg gttatgtgaa agaaccggaa      60
cgtggcctgt gggataacat tgtgtatctg gattttcgta gcctgnnncc gagcattatt     120
atcacccaca atgtgagccc ggataccctg aaccgtgaag gctgcaaaga atatgatgtg     180
gcgccggaag tgggccataa attctgcaaa gatttcccgg gctttatt                  228

<210> SEQ ID NO 2
<211> LENGTH: 500
<212> TYPE: DNA
<213> ORGANISM: Artificial Sequence
<220> FEATURE:
<223> OTHER INFORMATION: DNA template
<220> FEATURE:
<221> NAME/KEY: misc_feature
<222> LOCATION: (126)..(128)
<223> OTHER INFORMATION: N represents a degenerate position containing
      an equal distribution of A, T, G, and C nucleobases

<400> SEQUENCE: 2
aagatttccc gggctttatt ccgagcctgc tgggcgatct gctcgaggaa cgccagaaaa      60
```

```
tcaaacgcaa aatgaaagcg accgttgatc cgctggaaaa aaaactgctg gattatcgtc    120
agcgcnnnat taaaattctg gccaacagct tctatggcta ttatggttat gcgaaagcgc    180
gttggtattg caaagaatgc gcggaaagcg tgaccgcgtg gggccgtgaa tatatcgaaa    240
tggtgatccg cgagctcgaa gaaaaattcg gcttcaaagt gctgtatgcg gataccgatg    300
gcctgcatgc gaccattccg ggtgcggatg cggaaaccgt gaaaaaaaaa gcgaaagaat    360
tcctgaaata catcaatccg aaactgccgg gcctgctgga actggaatat gaaggctttt    420
atgtgcgtgg cttttcgtg accaaaaaaa aatacgcggt gatcgatgaa gaaggcaaaa    480
ttaccacccg tggcctggaa                                                500

<210> SEQ ID NO 3
<211> LENGTH: 495
<212> TYPE: DNA
<213> ORGANISM: Artificial Sequence
<220> FEATURE:
<223> OTHER INFORMATION: DNA template
<220> FEATURE:
<221> NAME/KEY: misc_feature
<222> LOCATION: (213)..(215)
<223> OTHER INFORMATION: N represents a degenerate position containing
      an equal distribution of A, T, G, and C nucleobases

<400> SEQUENCE: 3
aatacgcggt gatcgatgaa gaaggcaaaa ttaccacccg tggcctggaa attgtgcgtc     60
gtgattggag cgaaattgcg aaagaaaccc aggcgcgtgt gctggaagcg attctgaaac    120
atggcgatgt ggaagaagcg gtgcgtattg ttaaagaagt gaccgaaaaa ctgagcaaat    180
atgaggtacc gccggaaaaa ctggtgattc atnnncaaat tacccgtgat ctgcgtgatt    240
ataaagcgac cggtccgcat gtggcggtgg caaaacgtct ggcagcgcgt ggcgtgaaaa    300
ttcgtccggg caccgtgatt agctatattg tgctgaaagg cagcggccgc attggcgatc    360
gtgcgattcc ggcggatgaa tttgatccga ccaaacatcg ttatgatgcg gaatattata    420
tcgaaaacca ggtgctgccg gcggtggaac gtattctgaa agcgtttggc tatcgtaaag    480
aagatctgcg ctatc                                                     495

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
aactggcgcg ccgtcgtggc ggttatgcgg                                      30

<210> SEQ ID NO 5
<211> LENGTH: 39
<212> TYPE: DNA
<213> ORGANISM: Artificial Sequence
<220> FEATURE:
<223> OTHER INFORMATION: primer

<400> SEQUENCE: 5
cgttcctcga gcagatcgcc cagcaggctc ggaataaag                            39

<210> SEQ ID NO 6
<211> LENGTH: 32
<212> TYPE: DNA
<213> ORGANISM: Artificial Sequence
```

```
<220> FEATURE:
<223> OTHER INFORMATION: primer

<400> SEQUENCE: 6
atctgctcga ggaacgccag aaaatcaaac gc                                      32

<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
ttccaggcca cgggtggtaa ttttgc                                             26

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
aatacgcggt gatcgatgaa g                                                  21

<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9
gatagcgcag atcttcttta cgatagcc                                           28

<210> SEQ ID NO 10
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5' IRDye 800

<400> SEQUENCE: 10
gacactcgta tgcagtagcc                                                    20

<210> SEQ ID NO 11
<211> LENGTH: 80
<212> TYPE: DNA
<213> ORGANISM: Artificial Sequence
<220> FEATURE:
<223> OTHER INFORMATION: DNA template
<220> FEATURE:
<221> NAME/KEY: misc_feature
<222> LOCATION: (1)..(1)
<223> OTHER INFORMATION: 5' Cy3

<400> SEQUENCE: 11
acaaccatac tctcctcatc actattcaac ttacaatcga tacaaccttaa taatccacat       60 ggctactgca tacgagtgtc                                                    80

<210> SEQ ID NO 12
```

```
<211> LENGTH: 80
<212> TYPE: DNA
<213> ORGANISM: Artificial Sequence
<220> FEATURE:
<223> OTHER INFORMATION: DNA template
<220> FEATURE:
<221> NAME/KEY: misc_feature
<222> LOCATION: (1)..(1)
<223> OTHER INFORMATION: 5' 6-FAM

<400> SEQUENCE: 12
acaaccatac tctcctcatc actattcaac ttacaatcga tacaacctta taatccacat    60
ggctactgca tacgagtgtc                                                80

<210> SEQ ID NO 13
<211> LENGTH: 80
<212> TYPE: DNA
<213> ORGANISM: Artificial Sequence
<220> FEATURE:
<223> OTHER INFORMATION: DNA template

<400> SEQUENCE: 13
acaaccatac tctcctcatc actattcaac ttacaatcga tacaacctta taatccacat    60
ggctactgca tacgagtgtc                                                80

<210> SEQ ID NO 14
<211> LENGTH: 13
<212> TYPE: DNA
<213> ORGANISM: Artificial Sequence
<220> FEATURE:
<223> OTHER INFORMATION: probe

<400> SEQUENCE: 14
agagtatggt tgt                                                       13

<210> SEQ ID NO 15
<211> LENGTH: 16
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (16)..(16)
<223> OTHER INFORMATION: 3' Iowa Black FQ

<400> SEQUENCE: 15
aggagagtat ggttgt                                                    16

<210> SEQ ID NO 16
<211> LENGTH: 20
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (20)..(20)
<223> OTHER INFORMATION: 3' Iowa Black FQ

<400> SEQUENCE: 16
gatgaggaga gtatggttgt                                                20

<210> SEQ ID NO 17
<211> LENGTH: 13
<212> TYPE: DNA
<213> ORGANISM: Artificial Sequence
```

```
<220> FEATURE:
<223> OTHER INFORMATION: probe
<220> FEATURE:
<221> NAME/KEY: misc_feature
<222> LOCATION: (13)..(13)
<223> OTHER INFORMATION: 3' Black Hole Quencher-1

<400> SEQUENCE: 17
agagtatggt tgt                                                            13

<210> SEQ ID NO 18
<211> LENGTH: 16
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (16)..(16)
<223> OTHER INFORMATION: 3' Black Hole Quencher-1

<400> SEQUENCE: 18
aggagagtat ggttgt                                                         16

<210> SEQ ID NO 19
<211> LENGTH: 20
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (20)..(20)
<223> OTHER INFORMATION: 3' Black Hole Quencher.-1

<400> SEQUENCE: 19
gatgaggaga gtatggttgt                                                     20

<210> SEQ ID NO 20
<211> LENGTH: 90
<212> TYPE: DNA
<213> ORGANISM: Artificial Sequence
<220> FEATURE:
<223> OTHER INFORMATION: DNA template
<220> FEATURE:
<221> NAME/KEY: misc_feature
<222> LOCATION: (90)..(90)
<223> OTHER INFORMATION: 3' Inverted dT

<400> SEQUENCE: 20
tgtctacacg caagcttaca ttaagactcg ccatgttacg atctgccaag tacagccttg          60
aatcgtcact ggctactgca tacgagtgtc                                          90

<210> SEQ ID NO 21
<211> LENGTH: 40
<212> TYPE: DNA
<213> ORGANISM: Artificial Sequence
<220> FEATURE:
<223> OTHER INFORMATION: primer

<400> SEQUENCE: 21
cttttaagaa ccggacgaac gacactcgtt tgcagtagcc                               40

<210> SEQ ID NO 22
<211> LENGTH: 20
<212> TYPE: DNA
<213> ORGANISM: Artificial Sequence
<220> FEATURE:
```

```
<223> OTHER INFORMATION: primer

<400> SEQUENCE: 22
tgtctacacg caagcttaca                                              20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
cttttaagaa ccggacgaac                                              20

<210> SEQ ID NO 24
<211> LENGTH: 110
<212> TYPE: DNA
<213> ORGANISM: Artificial Sequence
<220> FEATURE:
<223> OTHER INFORMATION: fidelity assay reads

<400> SEQUENCE: 24
cttttaagaa ccggacgaac gacactcgtt tgcagtagcc ccattcttta acagctcatc   60
actagacatt tataagtcaa cattaacctc tgtctacacg caagcttaca             110

<210> SEQ ID NO 25
<211> LENGTH: 110
<212> TYPE: DNA
<213> ORGANISM: Artificial Sequence
<220> FEATURE:
<223> OTHER INFORMATION: fidelity assay reads

<400> SEQUENCE: 25
cttttaagaa ccggacgaac gacactcgtt tgcagtagcc ccattcttta acagctcatc   60
actagacatt tataagtcaa cattaacctc tgtctacacg caagcttaca             110

<210> SEQ ID NO 26
<211> LENGTH: 110
<212> TYPE: DNA
<213> ORGANISM: Artificial Sequence
<220> FEATURE:
<223> OTHER INFORMATION: fidelity assay reads

<400> SEQUENCE: 26
cttttaagaa ccggacgaac gacactcgtt tgcagtagcc ccattcttta acagctcatc   60
actagacatt tataagtcaa cattaacctc tgtctacacg caagcttaca             110

<210> SEQ ID NO 27
<211> LENGTH: 110
<212> TYPE: DNA
<213> ORGANISM: Artificial Sequence
<220> FEATURE:
<223> OTHER INFORMATION: fidelity assay reads

<400> SEQUENCE: 27
cttttaagaa ccggacgaac gacactcgtt tgcagtagcc ccattcttta acagctcatc   60
actagacatt tataagtcaa cattaacctc tgtctacacg caagcttaca             110

<210> SEQ ID NO 28
<211> LENGTH: 110
<212> TYPE: DNA
<213> ORGANISM: Artificial Sequence
```

```
<220> FEATURE:
<223> OTHER INFORMATION: fidelity assay reads

<400> SEQUENCE: 28
cttttaagaa ccggacgaac gacactcgtt tgcagtagcc ccattcttta acagctcatc      60
actagacatt tataagtcaa cattaacctc tgtctacacg caagcttaca                110

<210> SEQ ID NO 29
<211> LENGTH: 110
<212> TYPE: DNA
<213> ORGANISM: Artificial Sequence
<220> FEATURE:
<223> OTHER INFORMATION: fidelity assay reads

<400> SEQUENCE: 29
cttttaagaa ccggacgaac gacactcgtt tgcagtagcc ccattcttta acagctcatc      60
actagacatt tataagtcaa cattaacctc tgtctacacg caagcttaca                110

<210> SEQ ID NO 30
<211> LENGTH: 110
<212> TYPE: DNA
<213> ORGANISM: Artificial Sequence
<220> FEATURE:
<223> OTHER INFORMATION: fidelity assay reads

<400> SEQUENCE: 30
cttttaagaa ccggacgaac gacactcgtt tgcagtagcc ccattcttta acagctcatc      60
actagacatt tataagtcaa cattaacctc tgtctacacg caagcttaca                110

<210> SEQ ID NO 31
<211> LENGTH: 110
<212> TYPE: DNA
<213> ORGANISM: Artificial Sequence
<220> FEATURE:
<223> OTHER INFORMATION: fidelity assay reads

<400> SEQUENCE: 31
cttttaagaa ccggacgaac gacactcgtt tgcagtagcc ccattcttta acagctcatc      60
actagacatt tataagtcaa cattaacctc tgtctacacg caagcttaca                110

<210> SEQ ID NO 32
<211> LENGTH: 110
<212> TYPE: DNA
<213> ORGANISM: Artificial Sequence
<220> FEATURE:
<223> OTHER INFORMATION: fidelity assay reads

<400> SEQUENCE: 32
cttttaagaa ccggacgaac gacactcgtt tgcagtagcc ccattcttta acagctcatc      60
actagacatt tataagtcaa cattaacctc tgtctacacg caagcttaca                110

<210> SEQ ID NO 33
<211> LENGTH: 110
<212> TYPE: DNA
<213> ORGANISM: Artificial Sequence
<220> FEATURE:
<223> OTHER INFORMATION: fidelity assay reads

<400> SEQUENCE: 33
cttttaagaa ccggacgaac gacactcgtt tgcagtagcc ccattcttta acagctcatc      60
actagacatt tataagtcaa cattaacctc tgtctacacg caagcttaca                110
```

<210> SEQ ID NO 34
<211> LENGTH: 110
<212> TYPE: DNA
<213> ORGANISM: Artificial Sequence
<220> FEATURE:
<223> OTHER INFORMATION: fidelity assay reads

<400> SEQUENCE: 34
cttttaagaa ccggacgaac gacactcgtt tgcagtagcc ccattcttca acagctcatc    60
actagacatt tataagtcaa cattaacctc tgtctacacg caagcttaca             110

<210> SEQ ID NO 35
<211> LENGTH: 110
<212> TYPE: DNA
<213> ORGANISM: Artificial Sequence
<220> FEATURE:
<223> OTHER INFORMATION: fidelity assay reads

<400> SEQUENCE: 35
cttttaagaa ccggacgaac gacactcgtt tgcagtagcc ccattcttta acagctcatc    60
actagacatt tataagtcaa cattaacctc tgtctacacg caagcttaca             110

<210> SEQ ID NO 36
<211> LENGTH: 110
<212> TYPE: DNA
<213> ORGANISM: Artificial Sequence
<220> FEATURE:
<223> OTHER INFORMATION: fidelity assay reads

<400> SEQUENCE: 36
cttttaagaa ccggacgaac gacactcgtt tgcagtagcc ccattcttta acagctcatc    60
actagacatt tataagtcaa cattaacctc tgtctacacg caagcttaca             110

<210> SEQ ID NO 37
<211> LENGTH: 110
<212> TYPE: DNA
<213> ORGANISM: Artificial Sequence
<220> FEATURE:
<223> OTHER INFORMATION: fidelity assay reads

<400> SEQUENCE: 37
cttttaagaa ccggacgaac gacactcgtt tgcagtagcc ccattcttta acagctcatc    60
actagacatt tataagtcaa cattaatctc tgtctacacg caagcttaca             110

<210> SEQ ID NO 38
<211> LENGTH: 110
<212> TYPE: DNA
<213> ORGANISM: Artificial Sequence
<220> FEATURE:
<223> OTHER INFORMATION: fidelity assay reads

<400> SEQUENCE: 38
cttttaagaa ccggacgaac gacactcgtt tgcagtagcc ccattcttta acagctcatc    60
actagacatt tataagtcaa cattaacctc tgtctacacg caagcttaca             110

<210> SEQ ID NO 39
<211> LENGTH: 110
<212> TYPE: DNA
<213> ORGANISM: Artificial Sequence
<220> FEATURE:
<223> OTHER INFORMATION: fidelity assay reads

<400> SEQUENCE: 39

```
cttttaagaa ccggacgaac gacactcgtt tgcagtagcc ccattcttta acagctcatc    60
actagacatt tacaagtcaa cattaacctc tgtctacacg caagcttaca              110

<210> SEQ ID NO 40
<211> LENGTH: 110
<212> TYPE: DNA
<213> ORGANISM: Artificial Sequence
<220> FEATURE:
<223> OTHER INFORMATION: fidelity assay reads

<400> SEQUENCE: 40
cttttaagaa ccggacgaac gacactcgtt tgcagtagcc ccattcttta acagctcatc    60
actagacatt tataagtcaa cattaacctc tgtctacacg caagcttaca              110

<210> SEQ ID NO 41
<211> LENGTH: 110
<212> TYPE: DNA
<213> ORGANISM: Artificial Sequence
<220> FEATURE:
<223> OTHER INFORMATION: fidelity assay reads

<400> SEQUENCE: 41
cttttaagaa ccggacgaac gacactcgtt tgcagtagcc ccattcttta acagctcatc    60
actagacatt tataagtcaa cattaacctc tgtctacacg caagcttaca              110

<210> SEQ ID NO 42
<211> LENGTH: 110
<212> TYPE: DNA
<213> ORGANISM: Artificial Sequence
<220> FEATURE:
<223> OTHER INFORMATION: fidelity assay reads

<400> SEQUENCE: 42
cttttaagaa ccggacgaac gacactcgtt tgcagtagcc ccattcttta acagctcatc    60
actagacatt tataagtcaa cattaacctc tgtctacacg caagcttaca              110

<210> SEQ ID NO 43
<211> LENGTH: 110
<212> TYPE: DNA
<213> ORGANISM: Artificial Sequence
<220> FEATURE:
<223> OTHER INFORMATION: fidelity assay reads

<400> SEQUENCE: 43
cttttaagaa ccggacgaac gacactcgtt tgcagtagcc ccattcttta acagctcatc    60
actagacatt tataagtcaa cattaacctc tgtctacacg caagcttaca              110

<210> SEQ ID NO 44
<211> LENGTH: 110
<212> TYPE: DNA
<213> ORGANISM: Artificial Sequence
<220> FEATURE:
<223> OTHER INFORMATION: fidelity assay reads

<400> SEQUENCE: 44
cttttaagaa ccggacgaac gacactcgtt tgcagtagcc ccattcttta acagctcatc    60
actagacatt tataagtcaa cattaacctc tgtctacacg caagcttaca              110

<210> SEQ ID NO 45
<211> LENGTH: 110
<212> TYPE: DNA
```

```
<213> ORGANISM: Artificial Sequence
<220> FEATURE:
<223> OTHER INFORMATION: fidelity assay reads

<400> SEQUENCE: 45
cttttaagaa ccggacgaac gacactcgtt tgcagtagcc ccattcttta acagctcatc      60
actagacatt tataagtcaa cattaacccc tgtctacacg caagcttaca               110

<210> SEQ ID NO 46
<211> LENGTH: 110
<212> TYPE: DNA
<213> ORGANISM: Artificial Sequence
<220> FEATURE:
<223> OTHER INFORMATION: fidelity assay reads

<400> SEQUENCE: 46
cttttaagaa ccggacgaac gacactcgtt tgcagtagcc ccattcttta acagctcatc      60
actagacatt tataagtcaa cattaacctc tgtctacacg caagcttaca               110

<210> SEQ ID NO 47
<211> LENGTH: 110
<212> TYPE: DNA
<213> ORGANISM: Artificial Sequence
<220> FEATURE:
<223> OTHER INFORMATION: fidelity assay reads

<400> SEQUENCE: 47
cttttaagaa ccggacgaac gacactcgtt tgcagtagcc ccattcttta acagctcatc      60
actagacatt tataagtcaa cattaacctc tgtctacacg caagcttaca               110

<210> SEQ ID NO 48
<211> LENGTH: 110
<212> TYPE: DNA
<213> ORGANISM: Artificial Sequence
<220> FEATURE:
<223> OTHER INFORMATION: fidelity assay reads

<400> SEQUENCE: 48
cttttaagaa ccggacgaac gacactcgtt tgcagtagcc ccattcttta acagctcatc      60
actagacatt tataagtcaa caataacctc tgtctacacg caagcttaca               110
```